US007989434B2

(12) United States Patent
Feng

(10) Patent No.: US 7,989,434 B2
(45) Date of Patent: Aug. 2, 2011

(54) HETEROCYCLIC SELF-IMMOLATIVE LINKERS AND CONJUGATES

(75) Inventor: Bainian Feng, Foster City, CA (US)

(73) Assignee: Seattle Genetics, Inc., Bothell, WA (US)

( * ) Notice: Subject to any disclaimer, the term of this patent is extended or adjusted under 35 U.S.C. 154(b) by 0 days.

(21) Appl. No.: 12/764,821

(22) Filed: Apr. 21, 2010

(65) Prior Publication Data

US 2010/0273843 A1    Oct. 28, 2010

Related U.S. Application Data

(63) Continuation of application No. 11/925,659, filed on Oct. 26, 2007, now Pat. No. 7,754,681, which is a continuation of application No. 11/064,785, filed on Feb. 22, 2005, now Pat. No. 7,375,078.

(60) Provisional application No. 60/547,152, filed on Feb. 23, 2004.

(51) Int. Cl.
*A61K 31/395* (2006.01)
*A61K 31/435* (2006.01)
*A61K 31/495* (2006.01)
*A61K 31/53* (2006.01)
*C07K 16/00* (2006.01)

(52) U.S. Cl. ............... 514/79; 514/84; 514/85; 514/89; 530/387.1; 530/402; 530/403

(58) Field of Classification Search ............... None
See application file for complete search history.

(56) References Cited

U.S. PATENT DOCUMENTS

| | | | |
|---|---|---|---|
| 5,621,002 | A | 4/1997 | Bosslet et al. |
| 5,877,158 | A | 3/1999 | Bosslet et al. |
| 6,051,243 | A | 4/2000 | Bernardon |
| 6,214,345 | B1 | 4/2001 | Firestone et al. |
| 6,218,519 | B1 | 4/2001 | Kenten et al. |
| 6,268,488 | B1 | 7/2001 | Barbas, III et al. |
| 6,677,435 | B2 | 1/2004 | Rader et al. |
| 6,759,509 | B1 | 7/2004 | King et al. |
| 6,835,807 | B1 | 12/2004 | Susaki et al. |
| 7,091,186 | B2 | 8/2006 | Senter et al. |
| 7,521,541 | B2 | 4/2009 | Eigenbrot et al. |
| 7,553,816 | B2 | 6/2009 | Senter et al. |
| 7,575,748 | B1 | 8/2009 | Erickson et al. |
| 2003/0096743 | A1 | 5/2003 | Senter et al. |
| 2003/0130189 | A1 | 7/2003 | Senter et al. |
| 2003/0138432 | A1 | 7/2003 | Glazier |
| 2004/0018194 | A1 | 1/2004 | Francisco et al. |
| 2004/0052793 | A1 | 3/2004 | Carter et al. |
| 2004/0121940 | A1 | 6/2004 | De Groot et al. |
| 2004/0235068 | A1 | 11/2004 | Levinson |
| 2005/0169933 | A1 | 8/2005 | Steeves et al. |
| 2005/0238649 | A1 | 10/2005 | Doronina et al. |
| 2005/0276812 | A1 | 12/2005 | Ebens et al. |
| 2006/0074008 | A1 | 4/2006 | Senter et al. |
| 2006/0247295 | A1 | 11/2006 | Gangwar et al. |
| 2007/0092940 | A1 | 4/2007 | Eigenbrot et al. |
| 2007/0134243 | A1 | 6/2007 | Gazzard et al. |
| 2007/0269446 | A1 | 11/2007 | de Sauvage et al. |
| 2008/0085283 | A1 | 4/2008 | Levinson |
| 2008/0114153 | A1 | 5/2008 | Steeves et al. |
| 2008/0145374 | A1 | 6/2008 | Steeves et al. |
| 2008/0166294 | A1 | 7/2008 | de Sauvage et al. |
| 2008/0171040 | A1 | 7/2008 | Ebens et al. |
| 2008/0171856 | A1 | 7/2008 | Steeves et al. |
| 2008/0171865 | A1 | 7/2008 | Steeves et al. |
| 2008/0226659 | A1 | 9/2008 | Erickson et al. |
| 2009/0202536 | A1 | 8/2009 | Ebens et al. |

FOREIGN PATENT DOCUMENTS

| | | |
|---|---|---|
| WO | WO98013059 | 4/1998 |
| WO | WO02083180 | 10/2002 |
| WO | WO2004032828 | 4/2004 |

OTHER PUBLICATIONS

Carl et al., "A Novel Connector Linkage Applicable in Prodrug Design", J Med Chem., 24: 479-480 (1981).
Chakravarty et al., "Plasmin-Activated Prodrugs for Cancer Chemotherapy. 2. Synthesis and Biological Activity of Peptidyl Derivatives of Doxorubicin", J Med Chem, 26:638-644 (1983).
De Groot et al., "Elongated Multiple Electronic Cascade and Cyclization Spacer Systems in Activatible Anticancer Prodrugs for Enhanced Drug Release", J. Org. Chem., 66:8815-8830 (2001).
De Groot et al., "Design, Synthesis, and Biological Evaluation of a Dual Tumor-specific Motive Containing Integrin-targeted Plasmin-cleavable Doxorubicin Prodrug", Molecular Cancer Therapeutics, 1:901-911 (2002).
De Groot et al., "Synthesis and Biological Evaluation of Novel Prodrugs of Anthracyclines for Selective Activation by the Tumor-Associated Protease Plasmin", J. Med Chem, 42:5277-5283 (1999).
Devy et al., "Plasmin-activated doxorubicin prodrugs containing a spacer reduce tumor growth and angiogenesis without systemic toxicity", FASEB J.,18:565-7 (2004).
Doronina et al., "Development of potent monoclonal antibody auristatin conjugates for cancer therapy", Nature Biotechnology, 21:778-784 (2003).
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity", Bioconjugate Chem., 13:855-869 (2002).
Dubowchik et al., "Cathepsin B-Sensitive Dipeptide Prodrugs. 2. Models of Anticancer Drugs Paclitaxel (Taxol), Mitomycin C and Doxorubicin", Bioorg Med Chem Lett., 8:3347-3352 (1998).
Dubowchik et al., "Doxorubicin Immunoconjugates Containing Bivalent, Lysosomally-Cleavable Dipeptide Linkages", Bioorg Med Chem Lett, 12:1529-1532 (2002).

(Continued)

*Primary Examiner* — Christina Bradley

(57) ABSTRACT

The present invention provides heterocyclic linker compounds useful for linking drug moieties to ligands. The compounds also include drug-ligand conjugates comprising a ligand capable of targeting a selected cell population, and a drug connected to the ligand by a heterocyclic linker moiety. The linker moiety comprises a peptide sequence that is a substrate for an intracellular enzyme, for example a cathepsin, that cleaves the peptide at an amide bond. The peptide further contains a self-immolating moiety which connects the drug and the protein peptide sequence. Upon cleavage of the peptide sequence by an intracellular enzyme the self-immolating moiety cleaves itself from the drug moiety such that the drug moiety is in an underivatized and active form.

19 Claims, 2 Drawing Sheets

OTHER PUBLICATIONS

Dubowchik et al., "Efficient Mitomycin C Coupling with Stable p-Nitrophenyl-Benzyl Carbonates using N-Hydroxybenzotriazole as a Catalytic Additive", Tetrahedron Letters, 38:5261-5264 (1997).

Dubowchik et al., "Monomethoxytrityl (MMT) as a Versatile Amino Protecting Group for Complex Prodrugs of Anticancer Compounds Sensitive to Strong Acids, Bases and Nucleophiles", Tetrahedron Letters, 38:5257-5260 (1997).

Dubowchik, "Cathepsin B-Sensitive Dipeptide Prodrugs. 1. A Model Study of Structural Requirements for Efficient Release of Doxorubicin", Bioorg Med Chem Lett., 8:3341-3346 (1998).

Francisco et al., "cAC10-vcMMAE, an anti-CD30 Monomethyl Auristatin E Conjugate with Potent and Selective Antitumor Activity", Blood, 102:1458-1465 (2003).

Freshney, Culture of Animal Cells, A Manual of Basic Technique, Alan R. Liss, Inc., 1983, New York, p. 4.

Gura, "Systems for Identifying New Drugs are Often Faulty", Science 278:1041-2 (1997).

Hashimoto et al., "Significance of Cathepsin B Accumulation in Synovial Fluid of Rheumatoid Arthritis", Biochem Biophys Res Commun., 283:334-339 (2001).

Hay et al., "A 2-Nitromidazole Carbamate Prodrug of 5-Amino-1-(Chloromethyl)-3-[(5,6,7-Trimethoxyindol-2-YL]-1,2-Dihydro-3H-Benz [E] Indole (Amino-Seco-CBI-TMI) for Use with ADEPT and GDEPT", Bioorg Med Chem Lett., 9:2237-2242 (1999).

King et al., "Monoclonal Antibody Conjugates of Doxorubicin Prepared with Branched Peptide Linkers: Inhibition of Aggregation by Methoxytriethyleneglycol Chains", J Med Chem., 45:4336-4343 (2002).

Klussman et al., "Secondary mAb-vcMMAE Conjugates Are Highly Sensitive Reporters of Antibody Internalization via the Lysosome Pathway", Bioconjugate Chemistry, 15:765-773 (2004).

Shabat et al., "Chemical Adaptor Systems", Chemistry 10: 2626-2634 (2004).

Sinha et al., "Plasma Membrane Association of Cathepsin B in Human Prostate Cancer: Biochemical and Immunogold Electron Microscopic Analysis", Prostate, 49:172-184 (2001).

Walker et al., "Monoclonal antibody Mediated Intracellular Targeting of Tallysomycin S10b". Bioorganic & Medicinal Chemistry Letters, 14:4323-4327 (2004).

Zips et al., New Anticancer Agents: In Vitro and In Vivo Evaluation, In Vivo 19:1-8 (2005).

HETEROCYCLIC SELF-IMMOLATIVE LINKERS AND CONJUGATES

CROSS-REFERENCE TO RELATED APPLICATION

This non-provisional application filed under 37 CFR §1.53(b) is a continuation of U.S. patent application Ser. No. 11/925,659, filed Oct. 26, 2007, which is a continuation of U.S. Pat. No. 7,375,078, filed Feb. 22, 2005, issued May 20, 2008, which claims the benefit under 35 USC §119(e) of U.S. Provisional Application Ser. No. 60/547,152 filed on Feb. 23, 2004; the disclosures of which are incorporated herein by reference.

FIELD OF THE INVENTION

The present invention relates to heterocyclic linker compounds useful for linking drug moieties to ligands, and to drug-ligand conjugates in which the drug is enzymatically cleaved from the conjugate at a particular cell or tissue type targeted by said ligand.

BACKGROUND OF THE INVENTION

Targeted anti-cancer therapeutics are designed to reduce nonspecific toxicities and increase efficacy relative to conventional cancer chemotherapy. This approach is embodied by the powerful targeting ability of monoclonal antibodies to specifically deliver highly potent, conjugated small molecule therapeutics to a cancer cell. In an attempt to address the issue of toxicity, chemotherapeutic agents (drugs) have been coupled to targeting molecules such as antibodies or protein receptor ligands that bind with a high degree of specificity to tumor cells to form compounds referred to as antibody-drug conjugates (ADC) or immunoconjugates. Immunoconjugates in theory should be less toxic because they direct the cytotoxic drug to tumors that overexpress the particular cell surface antigen or receptor. This strategy has met limited success in part because cytotoxic drugs tend to be inactive or less active when conjugated to large antibodies or protein receptor ligands. Promising advancements with immunoconjugates has seen cytotoxic drugs linked to antibodies through a linker that is cleaved at the tumor site or inside tumor cells.

A chemical solution to targeted delivery of cytotoxic or cytostatic drugs conjugated to cell-specific ligands is the "self-immolative linker", PABC or PAB (para-aminobenzyloxycarbonyl), attaching the drug moiety to the ligand in the conjugate (Carl et al (1981) J. Med. Chem. 24:479-480; Chakravarty et al (1983) J. Med. Chem. 26:638-644). The PAB linker unit is also referred to as an electronic cascade spacer. The amide bond linking the carboxy terminus of a peptide unit and the para-aminobenzyl of PAB may be a substrate and cleavable by certain proteases. The aromatic amine becomes electron-donating and initiates an electronic cascade that leads to the expulsion of the leaving group, which releases the free drug after elimination of carbon dioxide (de Groot, et al (2001) Journal of Organic Chemistry 66(26):8815-8830). Cathepsin B is a ubiquitous cysteine protease. It is an intracellular enzyme, except in pathological conditions, such as metastatic tumors (Sinha et al (2001) Prostate 49:172-184) or rheumatoid arthritis (Hashimoto et al (2001) Biochem. Biophys. Res. Commun. 283:334-339). Therefore, conjugates produced with cathepsin B-cleavable linkers are likely to be stable in circulation. Upon cleavage of a peptide bond adjacent to the PABC, i.e. by an intracellular enzyme, the drug is released from the ligand whereby no remaining portion of the linker is bound (de Groot, et al (2002) Molecular Cancer Therapeutics 1(11):901-911; de Groot, et al (1999) J. Med. Chem. 42(25):5277-5283).

Linkers containing the para-aminobenzyloxycarbonyl (PAB or PABC) unit, in conjunction with a peptide unit, have been developed with a "self-immolating" or "self-immolative" mechanism of 1,6 elimination and fragmentation under enzymatic, hydrolytic, or other metabolic conditions to release a drug moiety from a targeting ligand, such as an antibody (U.S. Pat. No. 6,214,345; US20030130189; US20030096743; U.S. Pat. No. 6,759,509; US20040052793; U.S. Pat. Nos. 6,218,519; 6,835,807; 6,268,488; US20040018194; WO98/13059; US20040052793; U.S. Pat. Nos. 6,677,435; 5,621,002; US20040121940; WO2004/032828). The 2-nitroimidazol-5-ylmethyl group has been reported as a fragmenting prodrug unit (Hay et al. (1999) Bioorg. Med. Chem. Lett. 9:2237). For the use of the PAB unit in prodrugs and conjugates, see also: Walker, et al (2004) Bioorganic & Medicinal Chemistry Letters 14(16):4323-4327; Devy, et al (2004) FASEB Journal 18(3):565-567, 10.1096/fj.03-0462fje; Francisco, et al Blood (2003) 102(4):1458-1465; Doronina, et al (2003) Nature Biotechnology 21(7):778-784; King, et al (2002) Journal of Medicinal Chemistry 45(19):4336-4343; Dubowchik, et al (2002) Bioconjugate Chemistry 13(4):855-869; Dubowchik, et al (2002) Bioorganic & Medicinal Chemistry Letters 12(11):1529-1532.

Limitations of the PAB type self-immolating linkers are the propensity to cause poor solubility and aggregation of the conjugates. In addition, some PAB-containing conjugates may not be suitable substrates for certain cleaving enzymes or cleave too slowly to achieve efficacy. It would be desirable to improve the properties of drug-ligand conjugates by optimizing the structure of a self-immolative linker.

SUMMARY OF THE INVENTION

The present invention provides heterocyclic linker compounds selected from Formulas Ia, IIa and IIIa:

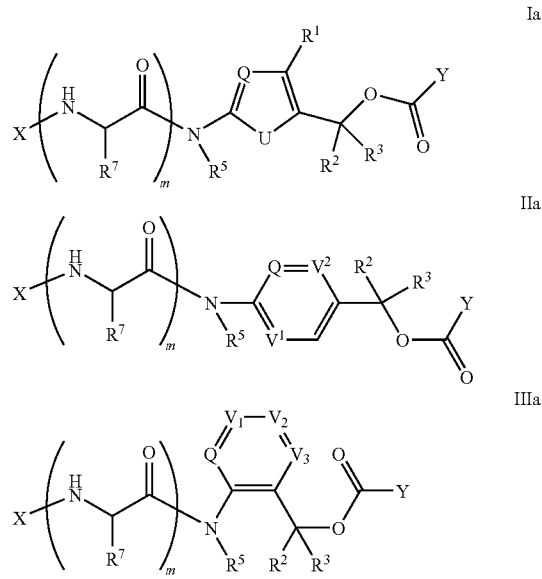

wherein
$R^7$ is the side chain of an amino acid and is optionally protected with a protecting group;
X and Y independently: are H, form a protecting group selected from Fmoc, Boc, triphenylmethyl, or form a reactive functional group selected from N-hydroxysuccinimide, para-nitrophenyl carbonate, para-nitrophenyl carbamate, pentafluorophenyl, haloacetamide, and maleimide; and m is 1, 2, 3, 4, 5, or 6.

Another aspect of the invention provides tissue specific, drug-ligand conjugates comprising a cell-specific ligand and a drug conjugated by a heterocyclic linker wherein said linker comprises a heterocyclic self-immolative moiety selected from Formulas I, II and III:

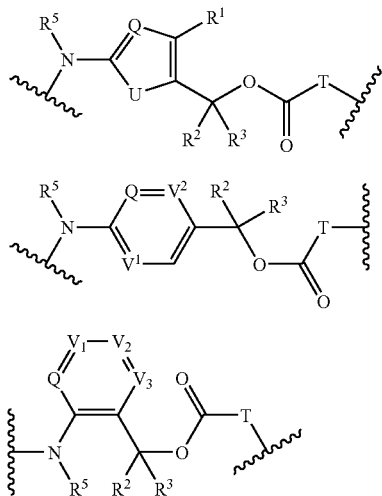

where the wavy lines indicate the covalent attachment sites to the cell-specific ligand and the drug moiety.

Another aspect of the invention provides ligand-drug conjugate compounds of Formula IV:

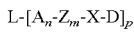

wherein

L is a cell-specific ligand capable of specifically targeting a selected cell population;

A is a Spacer unit;

Z is an Amino Acid;

X is a heterocyclic self-immolative moiety selected from formula I, II and III;

D is a drug moiety;

m is 1, 2, 3, 4, 5 or 6;

n is 0 or 1; and p is 1, 2, 3, 4, 5, 6, 7 or 8.

In another aspect, the present invention provides a method of treating a tumor in a mammal comprising administering an effective amount of a conjugate compound of the invention wherein the ligand of said conjugate binds to a tumor cell.

In another aspect of the invention, there is provided a method of killing a cell in a mammal comprising administering an effective amount of a conjugate compound of the invention.

DETAILED DESCRIPTION OF THE INVENTION

Figure 1:
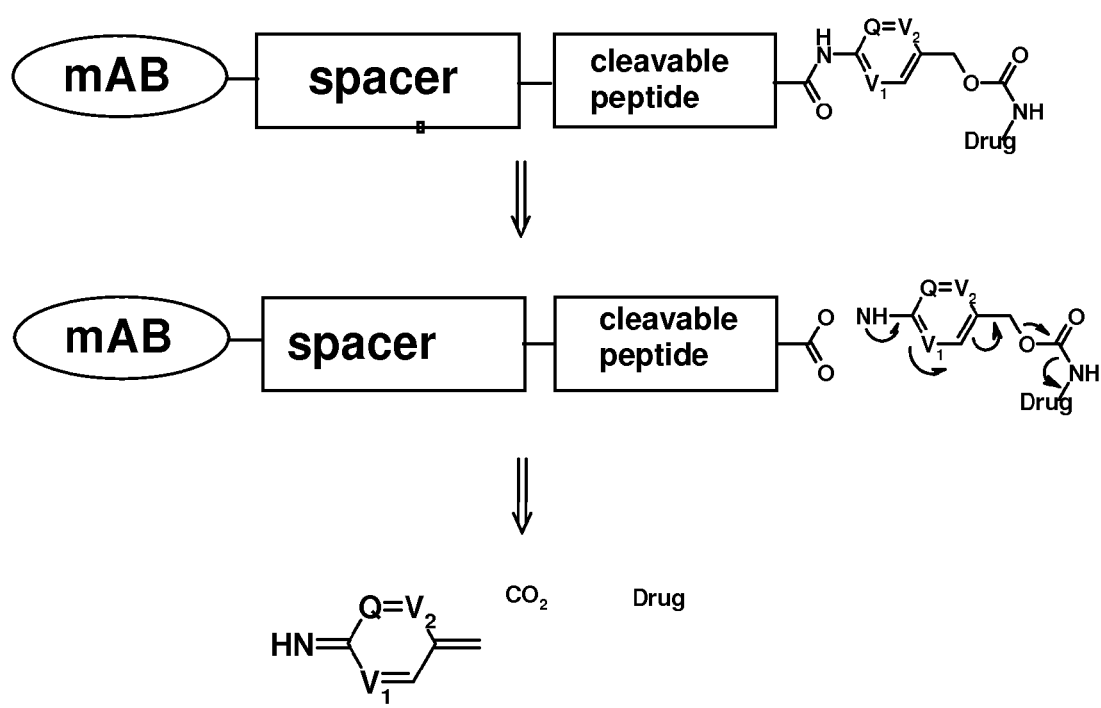
FIG. 1 is a schematic diagram illustrating the self-immolative mechanism of conjugates of the invention being cleaved by an enzyme.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

It will be understood that in the following detailed description and appended claims, the abbreviations and nomenclature employed are those which are standard in amino acid and peptide chemistry.

Definitions

Unless stated otherwise, the following terms and phrases as used herein are intended to have the following meanings:

The term "antibody" herein is used in the broadest sense and specifically covers monoclonal antibodies, polyclonal antibodies, multispecific antibodies (e.g., bispecific antibodies), and antibody fragments, so long as they exhibit the desired biological activity. Antibodies may be murine, human, humanized, chimeric, or derived from other species.

An antibody is a protein generated by the immune system that is capable of recognizing and binding to a specific antigen. (Janeway, et al (2001) "Immunobiology", 5th Ed., Garland Publishing, New York). A target antigen generally has numerous binding sites, also called epitopes, recognized by CDRs (complementary determining regions) on multiple antibodies. Each antibody that specifically binds to a different epitope has a different structure. Thus, one antigen may have more than one corresponding antibody.

The term "antibody," as used herein, also refers to a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; fragments produced by a Fab expression library, anti-idiotypic (anti-Id) antibodies, CDR, ECD (extracellular domain), and epitope-binding fragments of any of the above which immunospecifically bind to cancer cell antigens, viral antigens or microbial antigens, single-chain antibody molecules; and multispecific antibodies formed from antibody fragments.

An "intact antibody" herein is one comprising a VL and VH domains, as well as complete light and heavy chain constant domains.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) Nature 256:495, or may be made by recombinant DNA methods (see, U.S. Pat. No. 4,816,567). The "monoclonal antibodies" may also be isolated from phage antibody libraries using the techniques described in Clackson et al (1991) Nature, 352:624-628; Marks et al (1991) J. Mol. Biol., 222:581-597; for example.

As used herein, the term "chimeric antibody" refers to a monoclonal antibody comprising a variable region, i.e. binding region, from one source or species and at least a portion of a constant region derived from a different source or species, usually prepared by recombinant DNA techniques. Chimeric antibodies comprising a murine variable region and a human constant region are especially preferred in certain applications of the invention, particularly human therapy, because such antibodies are readily prepared and may be less immunogenic than purely murine monoclonal antibodies. Such murine/human chimeric antibodies are the product of expressed immunoglobulin genes comprising DNA segments encoding murine immunoglobulin variable regions and DNA segments encoding human immunoglobulin constant regions. Chimeric monoclonal antibodies may have specificity toward a tumor associated antigen. Other forms of chimeric antibodies encompassed by the invention are those in which the class or subclass has been modified or changed from that of the original antibody. Such "chimeric" antibodies are also referred to as "class-switched antibodies". Methods for producing chimeric antibodies involve conventional recombinant DNA and gene transfection techniques now well known in the art. See, e.g., Morrison, S. L, et al., Proc. Nat'l Acad. Sci., 81, 6851 (1984).

Encompassed by the term "chimeric antibody" is the concept of "humanized antibody", that is those antibodies in which the framework or "complementarity determining regions ("CDR") have been modified to comprise the CDR of an immunoglobulin of different specificity as compared to that of the parent immunoglobulin. In an exemplary embodiment, a murine CDR is grafted into the framework region of a human antibody to prepare the "humanized antibody". See, e.g., L. Riechmann et al., Nature 332, 323 (1988); M. S, Neuberger et al., Nature 314, 268 (1985). Exemplary CDRs correspond to those representing sequences recognizing the antigens noted above for the chimeric and bifunctional antibodies (EPA 0 239 400), incorporated herein by reference, for its teaching of CDR modified antibodies.

"Alkyl" is a $C_1$-$C_{18}$ hydrocarbon moiety containing normal, secondary, tertiary or cyclic carbon atoms. Examples of alkyl radicals include $C_1$-$C_8$ hydrocarbon moieties such as: methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, 1-heptyl, 1-octyl, cyclopropyl, cyclobutyl, cyclopentyl, cyclohexyl, cycloheptyl, and cyclooctyl.

"Alkenyl" is a $C_2$-$C_{18}$ hydrocarbon moiety containing normal, secondary, tertiary or cyclic carbon atoms with at least one site of unsaturation, i.e. a carbon-carbon, $sp^2$ double bond. Examples of alkenyl radicals include $C_2$-$C_8$ hydrocarbon moieties such as, but not limited to: ethylene or vinyl (—CH=$CH_2$), allyl (—$CH_2$CH=$CH_2$), 1-cyclopent-1-enyl, 1-cyclopent-2-enyl, 1-cyclopent-3-enyl, 5-hexenyl (—$CH_2CH_2CH_2CH_2$CH=$CH_2$), 1-cyclohex-1-enyl, 1-cyclohex-2-enyl, and 1-cyclohex-3-enyl.

"Alkynyl" is a $C_2$-$C_{18}$ hydrocarbon moiety containing normal, secondary, tertiary or cyclic carbon atoms with at least one site of unsaturation, i.e. a carbon-carbon, sp triple bond. Examples of alkynyl radicals include $C_2$-$C_8$ hydrocarbon moieties such as, but not limited to: acetylenic (—C≡CH) and propargyl (—$CH_2$C≡CH).

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Examples of alkylene radicals include $C_1$-$C_8$ hydrocarbon moieties such as, but not limited to: methylene (—$CH_2$—) 1,2-ethyl (—$CH_2CH_2$—), 1,3-propyl (—$CH_2CH_2CH_2$—), 1,4-butyl (—$CH_2CH_2CH_2CH_2$—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Examples of alkenylene radicals include $C_2$-$C_8$ hydrocarbon moieties such as, but not limited to: 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Examples of alkynylene radicals include $C_2$-$C_8$ hydrocarbon moieties such as, but not limited to: acetylene (—C≡C—), propargyl (—$CH_2$C≡C—), and 4-pentynyl (—$CH_2CH_2CH_2$C≡CH—).

"Aryl" means a monovalent aromatic hydrocarbon radical of 6-20 carbon atoms derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, naphthalene, anthracene, biphenyl, and the like.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms.

"Heteroarylalkyl" refers to an acyclic alkyl radical in which one of the hydrogen atoms bonded to a carbon atom, typically a terminal or $sp^3$ carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g. the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo [4,5], [5,5], [5,6], or [6,6] system.

"Substituted alkyl", "substituted aryl", and "substituted arylalkyl" mean alkyl, aryl, and arylalkyl respectively, in which one or more hydrogen atoms are each independently replaced with a substituent. Typical substituents include, but are not limited to, —X, —R, —O⁻, —OR, —SR, —S⁻, —NR$_2$, —NR$_3$, =NR, —CX$_3$, —CN, —OCN, —SCN, —N=C=O, —NCS, —NO, —NO$_2$, =N$_2$, —N$_3$, —NC(=O)R, —C(=O)R, —C(=O)NR$_2$, —SO$_3^-$, —SO$_3$H, —S(=O)$_2$R, —OS(=O)$_2$OR, —S(=O)$_2$NR, —S(=O)R, —OP(=O)(OR)$_2$, —P(=O)(OR)$_2$, —PO$^-_3$, —PO$_3$H$_2$, —C(=O)R, —C(=O)X, —C(=S)R, —CO$_2$R, —CO$_2^-$, —C(=S)OR, —C(=O)SR, —C(=S)SR, —C(=O)NR$_2$, —C(=S)NR$_2$, —C(=NR)NR$_2$, where each X is independently a halogen: F, Cl, Br, or I; and each R is independently H, $C_1$-$C_{18}$ alkyl, $C_6$-$C_{20}$ aryl, $C_3$-$C_{14}$ heterocycle, or protecting group. Alkylene, alkenylene, and alkynylene groups as described above may also be similarly substituted.

"Heteroaryl", "heterocyclyl", and "heterocycle" all refer to a ring system in which one or more ring atoms is a heteroatom, e.g. nitrogen, oxygen, and sulfur. The heterocycle radical comprises 1 to 20 carbon atoms and 1 to 5 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4Ah-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" and "carbocyclyl" mean a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl.

"Reactive functional groups" include, but are not limited to, olefins, acetylenes, alcohols, phenols, ethers, oxides, halides, aldehydes, ketones, carboxylic acids, esters, carbonates, amides, cyanates, isocyanates, thiocyanates, isothiocyanates, amines, hydrazines, hydrazones, hydrazides, diazo, diazonium, nitro, nitriles, mercaptans (thiols), sulfides, disulfides, sulfoxides, sulfones, sulfonic acids, sulfinic acids, acetals, ketals, anhydrides, sulfates, sulfenic acids, isonitriles, amidines, imides, imidates, nitrones, hydroxylamines, oximes, hydroxamic acids, thiohydroxamic acids, allenes, orthoesters, sulfites, enamines, ynamines, ureas, pseudoureas, semicarbazides, carbodiimides, carbamates, imines, azides, azo compounds, azoxy compounds, and nitroso compounds. Exemplary reactive functional groups include N-hydroxysuccinimide (NHS)esters, para-nitrophenyl (PNP) carbonates, pentafluorophenyl (PFP) carbonates, and maleimides. See: Sandler and Karo, Eds. "Organic Functional Group Preparations", Academic Press, San Diego, 1989.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBz) and 9-fluorenylmethylenoxycarbonyl (Fmoc) Similarly, a "hydroxy-protecting group" refers to a substituent of a hydroxy group that blocks or protects the hydroxy functionality. Suitable protecting groups include acetyl, benzyl, benzoyl, tetrahydropyranyl, and trialkylsilyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

"Linker", "Linker Unit", or "link" means a chemical moiety comprising a covalent bond or a chain of atoms that covalently attaches an antibody to a drug moiety. Exemplary linker abbreviations include: MC=6-maleimidocaproyl, MP=maleimidopropanoyl, val-cit=valine-citrulline, dipeptide site in protease-cleavable linker, ala-phe=alanine-phenylalanine, dipeptide site in protease-cleavable linker, PAB=p-aminobenzyloxycarbonyl, SPP=N-Succinimidyl 4-(2-pyridylthio) pentanoate, SMCC=N-Succinimidyl 4-(N-maleimidomethyl)cyclohexane-1 carboxylate, SIAB=N-Succinimidyl (4-iodo-acetyl)aminobenzoate.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable minor images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and 1 or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are minor images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The abbreviations used in the present application, unless otherwise indicated are as follows: AcOH: acetic acid; Ala: L-alanine; Alloc: allyloxy-carbonyl; Arg: L-arginine; Boc: t-butyloxycarbonyl; Cit: L-citrulline; CDI: N,N-carbonyldiimidazole; DBU: diazobicycloundecene; DCC: dicyclohexylcarbodiimide; DCI: direct chemical ionization; DCU: dicyclohexylurea; DIEA: diisopropylethylamine; DMAP: 4-dimethylaminopyridine; DME: 1,2-dimethoxyethane; DOX: doxorubicin; DTT: dithiothreitol; EEDQ: N-ethoxycarbonyl-2-ethoxy-1,2-dihydroquinoline; EtOAc: ethyl acetate; Fmoc: fluorenylmethoxycarbonyl; GABA: γ-aminobutyric acid; Gly: glycine; HOBt: N-hydroxybenzotriazole; HRMS: high resolution mass spectroscopy; Ile: L-isoleucine; LAH: lithium aluminum hydride; Leu: L-leucine; Lys: L-lysine; MC: 6-maleimidocaproyl; MMA: mitomycin A, MMC: mitomycin C; Mtr: 4-methoxytrityl; NHS: N-hydroxysuccinimide; NMP: N-methylpyrrolidinone; PABC: p-aminobenzyl-carbamoyl; PAB-OH: p-aminobenzyl alcohol; Phe:L-phenylalanine; PNP: p-nitrophenol; PNPCF: p-nitrophenylchloroformate TFA: trifluoroacetic acid; THF: tetrahydrofuran; Trp: L-tryptophan; Val: L-valine; Z: benzyloxycarbonyl.

Heterocyclic Self-Immolative Linked Conjugates

The present invention provides novel drug-ligand conjugates comprising a ligand capable of targeting a selected cell population, and a drug connected to the ligand by a linker moiety. The linker moiety comprises a heterocyclic "self-immolating moiety" of Formulas I, II or III bound to the drug and incorporates an amide group that upon hydrolysis by an intracellular protease initiates a reaction that ultimately cleaves the self-immolative moiety from the drug such that the drug is released from the conjugate in an active form. The linker moiety further comprises a peptide sequence adjacent to the self-immolative moiety that is a substrate for an intracellular enzyme, for example a cathepsin such as cathepsin B, that cleaves the peptide at the amide bond shared with the self-immolative moiety. The ligand molecule can be an immunoreactive protein such as an antibody, or fragment thereof, a non-immunoreactive protein, or peptide ligand such as bombesin or, a binding ligand recognizing a cell associated receptor such as a lectin, or any protein or peptide that possesses a reactive functional group such as an amine (—$NH_2$), aldehyde (—CHO), carboxyl (—COOH) or a sulfhydryl group (—SH), or else can be modified to contain such a functional group. The spacer unit is linked to the ligand via an amide, amine or thioether bond. The drug moiety is connected to the self-immolative moiety of the linker via a chemically reactive functional group pending from the drug such as a primary or secondary amine, hydroxyl, sulfhydryl or carboxyl group.

A conjugate of the present invention is represented by general Formula IV:

$$L-[A_n-Z_m-X-D]_p \qquad \text{IV}$$

in which L is a cell-specific ligand capable of specifically targeting a selected cell population, D is a drug moiety, and [A-$Z_m$-X] is the linker wherein A is optionally present as a spacer unit (n is 0 or 1), $Z_m$ is an enzymatically cleavable peptide (amino acid) sequence (m is 1, 2, 3, 4, 5 or 6), and X is a heterocyclic self-immolating group connecting the drug moiety D and the enzymatically cleavable peptide sequence Z. The number of drug moieties per ligand, i.e. drug loading value p, is 1 to about 8. The heterocyclic self-immolating group X is selected from Formulas I, II and III;

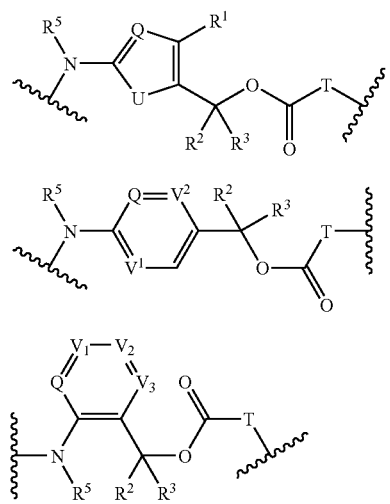

where the wavy lines indicate the covalent attachment sites to the cell-specific ligand and the drug moiety, and wherein:

U is O, S or $NR^6$;

Q is $CR^4$ or N;

$V^1$, $V^2$ and $V^3$ are independently $CR^4$ or N provided that for formula II and III at least one of Q, $V^1$ and $V^2$ is N;

T is NH, $NR^6$, O or S pending from said drug moiety;

$R^1$, $R^2$, $R^3$ and $R^4$ are independently selected from H, F, Cl, Br, I, OH, —N($R^5$)$_2$, —N($R^5$)$_3^+$, $C_1$-$C_8$ alkylhalide, carboxylate, sulfate, sulfamate, sulfonate, —$SO_2R^5$, —S(=O)$R^5$, —$SR^5$, —$SO_2N(R^5)_2$, —C(=O)$R^5$, —$CO_2R^5$, —C(=O)N($R^5$)$_2$, —CN, —$N_3$, —$NO_2$, $C_1$-$C_8$ alkoxy, $C_1$-$C_8$ halosubstituted alkyl, polyethyleneoxy, phosphonate, phosphate, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_1$-$C_{20}$ heterocycle, and $C_1$-$C_{20}$ substituted heterocycle; or when taken together, $R^2$ and $R^3$ form a carbonyl (=O), or spiro carbocyclic ring of 3 to 7 carbon atoms; and $R^5$ and $R^6$ are independently selected from H, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_1$-$C_{20}$ heterocycle, and $C_1$-$C_{20}$ substituted heterocycle;

where $C_1$-$C_8$ substituted alkyl, $C_2$-$C_8$ substituted alkenyl, $C_2$-$C_8$ substituted alkynyl, $C_6$-$C_{20}$ substituted aryl, and $C_2$-$C_{20}$ substituted heterocycle are independently substituted with one or more substituents selected from F, Cl, Br, I, OH, —N($R^5$)$_2$, —N($R^5$)$_3^+$, $C_1$-$C_8$ alkylhalide, carboxylate, sulfate, sulfamate, sulfonate, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, —$SO_2R^5$, —S(=O)$R^5$, —$SR^S$, —$SO_2N(R^5)_2$, —C(=O)$R^5$, —$CO_2R^5$, —C(=O)N($R^5$)$_2$, —CN, —$N_3$, —$NO_2$, $C_1$-$C_8$ alkoxy, $C_1$-$C_8$ trifluoroalkyl, $C_1$-$C_8$ alkyl, $C_3$-$C_{12}$ carbocycle, $C_6$-$C_{20}$ aryl, $C_2$-$C_{20}$ heterocycle, polyethyleneoxy, phosphonate, and phosphate.

Heterocyclic Self-Immolative Moiety (X)

The drug-ligand conjugates of the invention employ a heterocyclic self-immolative moiety (X) covalently linked to the drug moiety and the cleavable peptide sequence moiety. A self-immolative moiety may be defined as a bifunctional chemical group which is capable of covalently linking together two spaced chemical moieties into a normally stable molecule, releasing one of said spaced chemical moieties from the molecule by means of enzymatic cleavage; and following said enzymatic cleavage, spontaneously cleaving from the remainder of the bifunctional chemical group to release the other of said spaced chemical moieties. In accordance with the present invention, the self-immolative moiety is covalently linked at one of its ends, directly or indirectly through a Spacer unit, to the ligand by an amide bond and covalently linked at its other end to a chemical reactive site (functional group) pending from the drug. The derivatization of the drug with the self-immolative moiety may render the drug less pharmacologically active (e.g. less toxic) or not active at all until the drug is cleaved.

The conjugate is stable extracellularly, or in the absence of an enzyme capable of cleaving the amide bond of the self-immolative moiety. However, upon entry into a cell, or exposure to a suitable enzyme, the amide bond is cleaved initiating a spontaneous self-immolative reaction resulting in the cleavage of the bond covalently linking the self-immolative moiety to the drug, to thereby effect release of the drug in its underivatized or pharmacologically active form. In one embodiment, the self-immolative linker is coupled to the ligand, through an enzymatically cleavable peptide sequence that provides a substrate for an intracellular enzyme to cleave the amide bond to initiate the self-immolative reaction.

The self-immolative moiety in conjugates of the invention either incorporate one or more heteroatoms and thereby provides improved solubility, improves the rate of cleavage and decreases propensity for aggregation of the conjugate. These improvements of the heterocyclic self-immolative linker constructs of the present invention over non-heterocyclic, PAB-type linkers may result in surprising and unexpected biological properties such as increased efficacy, decreased toxicity, and more desirable pharmacokinetics.

It will be understood that when T is NH, it is derived from a primary amine (—$NH_2$) pending from the drug moiety (prior to coupling to the self-immolative moiety) and when T is N, it is derived from a secondary amine (—NH—) from the drug moiety (prior to coupling to the self-immolative moiety). Similarly, when T is O or S, it is derived from a hydroxyl (—OH) or sulfhydryl (—SH) group respectively pending from the drug moiety prior to coupling to the self-immolative moiety.

Not to be limited by theory or a particular mechanism, the presence of electron-withdrawing groups on the heterocyclic ring of formula I, II or III linkers may moderate the rate of cleavage. FIG. 1 is a schematic diagram illustrating the self-immolative mechanism of conjugates of the invention being cleaved by an enzyme.

In one embodiment, the self-immolative moiety is the group of formula I in which Q is N, and U is O or S. Such group has a non-linearity structural feature which improves solubility or the conjugates. In this context R may be H, methyl, nitro, or CF$_3$ while T is N or NH pending from the drug moiety D. In one embodiment, Q is N and U is O thereby forming an oxazole ring and R is H. In another embodiment, Q is N and U is S thereby forming a thiazole ring optionally substituted at R with an Me or CF$_3$ group and T is N or NH pending from drug moiety D. It will be understood that when T is NH, it is derived from a primary amine (—NH$_2$) pending from the drug moiety (prior to coupling to the self-immolative moiety) and when T is N, it is derived from a secondary amine (—NH—) from the drug moiety (prior to coupling to the self-immolative moiety). Similarly, when T is O or S, it is derived from a hydroxyl (—OH) or sulfhydryl (—SH) group respectively pending from the drug moiety prior to coupling to the self-immolative moiety.

In another exemplary embodiment, the self-immolative moiety is the group of formula II in which Q is N and V$^1$ and V$^2$ are independently N or CH and T is N or NH. In another embodiment, Q, V$^1$ and V$^2$ are each N. In another embodiment, Q and V$^1$ are N while V$^2$ is CH. In another embodiment, Q and V$^2$ are N while V$^1$ is CH.

In another embodiment, Q and V$^1$ are both CH and V$^2$ is N. In another embodiment, Q is N while V$^1$ and V$^2$ are both CH.

In another embodiment, the self-immolative moiety is the group of formula III in which Q, V$^1$, V$^2$ and V$^3$ are each independently N or CH and T is N or NH. In another embodiment Q is N while V$^1$, V$^2$ and V$^3$ are each N. In another embodiment, Q V$^1$, and V$^2$ are each CH while V$^3$ is N. In another embodiment Q, V$^2$ and V$^3$ are each CH while V$^1$ is N. In another embodiment, Q, V$^1$ and V$^3$ are each CH while V$^2$ is N. In another embodiment, Q and V$^2$ are both N while V$^1$ and V$^3$ are both CH. In another embodiment Q and V$^2$ are both CH while V$^1$ and V$^3$ are both N. In another embodiment, Q and V$^3$ are both N while V$^1$ and V$^2$ are both CH.

Cleavable Peptide Sequence (Z$_M$)

In the conjugate of Formula IV, each m is independently 1, 2, 3, 4, 5 or 6. In exemplary embodiments, m may be 1, 2 or 3, to form single amino acid, dipeptide, and tripeptide amino acid units, respectively Amino acid units Z are selected from natural and non-natural amino acids. The side chain-bearing carbon may be in either D or L (R or S) configuration Amino acid unit Z may be alanine, 2-amino-2-cyclohexylacetic acid, 2-amino-2-phenylacetic acid, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, γ-aminobutyric acid, α,α-dimethyl γ-aminobutyric acid, β,β-dimethyl γ-aminobutyric acid, ornithine, and citrulline (Cit) Amino acid unit Z optionally includes protected forms of amino acids where reactive functionality of the side chains are protected. Protected amino acid reagents and intermediates are well known, including lysine-protected with acetyl, formyl, triphenylmethyl (trityl), and monomethoxytrityl (MMT). Other protected amino acid units include arginine-protected tosyl or nitro group, ornithine-protected with acetyl or formyl groups.

Each Z$_m$ unit independently has the formula denoted below in the square brackets, where m is an integer ranging from 0 to 6:

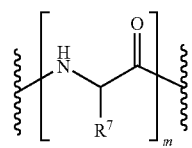

wherein R$^7$ includes, but is not limited to, hydrogen, methyl, isopropyl, isobutyl, sec-butyl, phenyl, benzyl, p-hydroxybenzyl, —CH$_2$OH, —CH$_2$SH, —CH$_2$CH$_2$OH, —CH$_2$CH$_2$SH, —CH(OH)CH$_3$, —CH$_2$SCH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl-, phenyl, cyclohexyl,

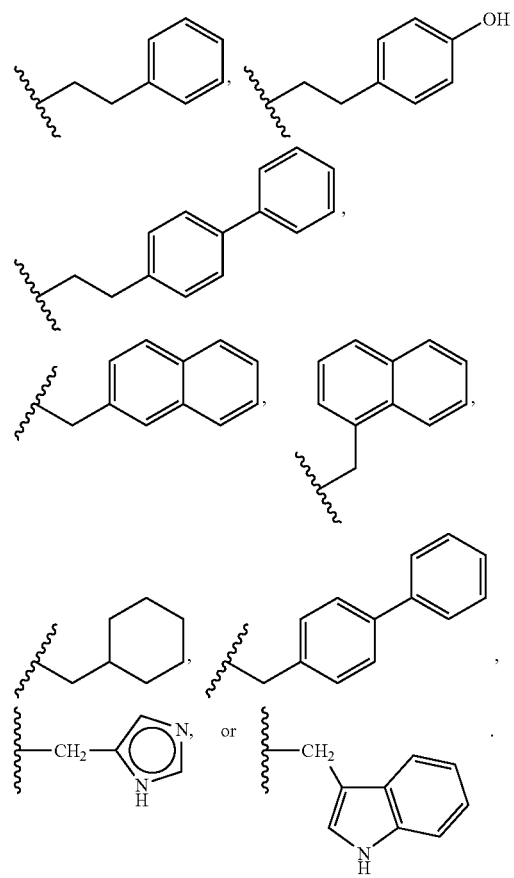

The peptide unit sequence Z$_m$ is specifically tailored so that it will be selectively enzymatically cleaved from the drug moiety by one or more of the cellular proteases. The amino acid residue chain length of the peptide linker ranges from that of a single amino acid to about eight amino acid residues. The following are exemplary enzymatically-cleavable peptide sequences of the invention: Gly-Gly, Phe-Lys, Val-Lys, Phe-Phe-Lys, D-Phe-Phe-Lys, Gly-Phe-Lys, Ala-Lys, Val-Cit, Phe-Cit, Leu-Cit, Ile-Cit, Trp-Cit, Phe-Ala, Ala-Phe, Gly-Gly-Gly, Gly-Ala-Phe, Gly-Val-Cit, Gly-Phe-Leu-Gly, Ala-Leu-Ala-Leu, Phe-N 9-tosyl-Arg, and Phe-N 9-Nitro-Arg, in either orientation. Numerous specific cleavable peptide sequences suitable for use in the present invention can be designed and optimized in their selectivity for enzymatic cleavage by a particular intracellular enzyme e.g. a tumor-associated protease. Cleavable peptides for use in the present invention include those which are optimized toward the proteases, cathepsin B, C and D, such as Phe-Lys, Ala-Phe, and Val-Cit. Another peptide sequence for use in the present invention is tripeptide D-Ala-Phe-Lys, which is selectively recognized by the tumor-associated protease plasmin, which is involved in tumor invasion and metastasis (de Groot, et al (2002) Molecular Cancer Therapeutics 1(11):901-911; de Groot, et al (1999) J. Med. Chem. 42(25):5277-5283).

Each carbon atom to which $R^7$ is attached independently in the (S) or (R) configuration, or a racemic mixture Amino acid units may thus be enantiomerically pure, racemic, or diastereomeric.

Spacer Unit (A)

In an exemplary embodiment, conjugates of Formulas IV optionally incorporate a spacer unit "A" (i.e. n is 1) which is a divalent moiety that couples the N-terminus of the cleavable peptide ($Z_m$) to the ligand L. The spacer unit is of a length that enables the cleavable peptide sequence to be contacted by the cleaving enzyme (e.g. cathepsin B) and the hydrolysis of the amide bond coupling the cleavable peptide to the self-immolative moiety X. Spacer unit A is covalently bound to $Z_m$ via an amide bond. Alternatively, the spacer unit is a bond and ligand L is directly and covalently attached to the self-immolative moiety X. In this case, the ligand L and the self-immolative moiety X form an amide bond that upon proteolytic cleavage initiates the self-immolative reaction and the ultimate release of the drug D.

The spacer unit A is covalently bound to a functional group pending from the ligand L such as an amine (e.g. —$NH_2$ from a Lys residue), a carboxyl (—COOH from an Asp or Glu residue) or a sulfhydryl (e.g. —SH from a Cys residue) which forms an amide or a thioether or disulfide group. Spacer units may comprise a divalent radical such as an alkyldiyl, an aryldiyl, a heteroaryldiyl, moieties such as: —$(CR_2)_nO$ $(CR_2)_n$—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide.

Conjugates of the invention in which the spacer unit A is reacted with a sulfhydryl functional group of ligand L (for example when L is Cys containing peptide or a reduced antibody) to form a thioether linkage include those represented by Formulas Va-Ve), in which spacer unit "A" is the compound in brackets.

Va

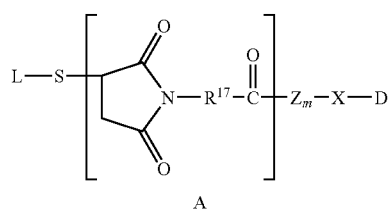

A in which $R^{17}$ is selected from $(CH_2)_r$, $C_3$-$C_8$ carbocyclyl, O—$(CH_2)_r$, arylene, $(CH_2)_r$-arylene, -arylene-$(CH_2)_r$—, $(CH_2)_r$—$(C_3$-$C_8$ carbocyclyl), —$(C_3$-$C_8$ carbocyclyl)-$(CH_2)_r$, $C_3$-$C_8$ heterocyclyl, $(CH_2)_r$—$(C_3$-$C_8$ heterocyclyl), —$(C_3$-$C_8$ heterocyclyl)-$(CH_2)_r$—, —$(CH_2)_rC(O)NR^b(CH_2)_r$—, —$(CH_2CH_2O)_r$—, —$(CH_2CH_2O)_r$—$CH_2$—, —$(CH_2)_rC(O)NR^b$ $(CH_2CH_2O)_r$—, —$(CH_2)_rC(O)NR^b(CH_2CH_2O)_r$—$CH_2$—, —$(CH_2CH_2O)_rC(O)NR^b(CH_2CH_2O)_r$—, —$(CH_2CH_2O)_nC(O)NR^b(CH_2CH_2O)_r$—$CH_2$—, and —$(CH_2CH_2O)_rC(O)NR^b(CH_2)_r$—; where r is independently an integer ranging from 1-10. L, Y, Z, X, D, and m are as previously defined.

An illustrative Spacer unit A is that of Formula Va includes maleimidocaproyl (MC), where $R^{17}$ is —$(CH_2)_5$—, made from maleimidocaproyl-N-hydroxysuccinimide (MC-NHS):

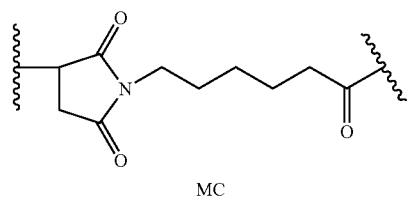

MC

An illustrative Spacer unit A is that of Formula Va is derived from maleimido-propanoyl (MP) wherein $R^{17}$ is —$(CH_2)_2$—:

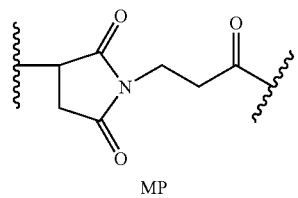

MP

Another illustrative Spacer unit A is that of Formula Va wherein $R^{17}$ is —$(CH_2CH_2O)_r$—$CH_2$— and r is 2:

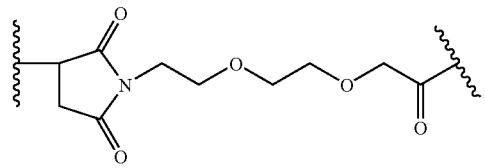

Another illustrative Spacer unit A is that of Formula Va wherein $R^{17}$ is —$(CH_2)_rC(O)NR^b(CH_2CH_2O)_r$—$CH_2$— where $R^b$ is H and each r is 2:

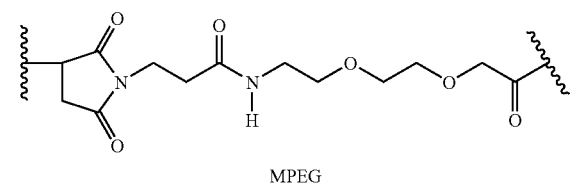

MPEG

Another exemplary spacer unit is SMCC as in Vb, made from succinimidyl 4-(N-maleimidomethyl)-cyclohexane-1-carboxylate (SMCC, Pierce Catalog):

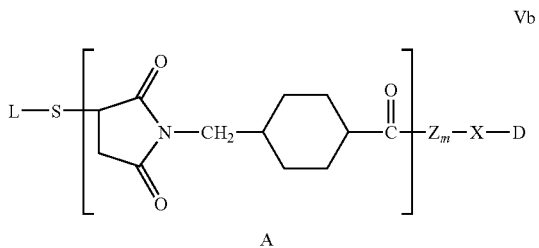

Vb

Another exemplary spacer unit is made from m-maleimidobenzoyl-N-hydroxysuccinimide ester (MBS) (Pierce Catalog p. E-16 (1992)), as in Vc:

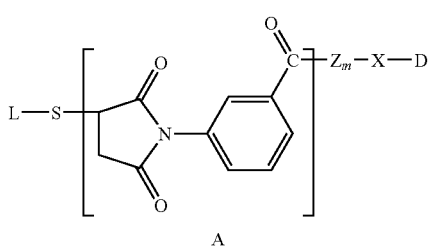

Vc

Another exemplary spacer unit is made from succinimidyl 4-(p-maleimidophenyl)butyrate (SMPB, Pierce catalog), as in Vd:

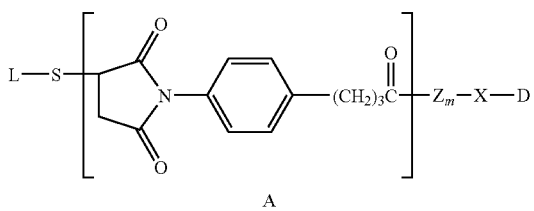

Vd

Another exemplary spacer unit is made from N-succinimidyl(4-iodoacetyl)aminobenzoate (SIAB, Pierce Biotechnology, Inc.), as in Ve:

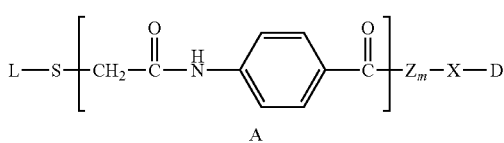

Ve

Other conjugates in which spacer unit A and ligand L are linked via a thioether group may be prepared by reacting a sulfhydryl functional group pending from ligand L with an activated disulfide-containing precursor of spacer unit A. Representative of conjugates of this type are Formulas VIa-d.

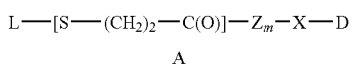

VIa

Another exemplary spacer unit is made from 4-succinimidyloxycarbonyl-α-methyl-α-(2-pyridyldithio)toluene (SMPT, Pierce Biotechnology, Inc.), as in VIb:

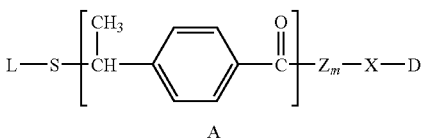

VIb

Another exemplary spacer unit made from succinimidyl 6-[3-(2-pyridyldithio)-propionamide]hexanoate (LC-SPDP, Pierce Biotechnology, Inc) as shown in VIc:

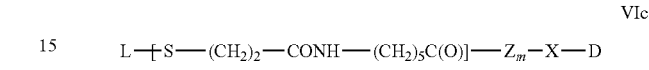

VIc

Another exemplary spacer unit is made from a haloacetamide reagent, as shown in VIc:

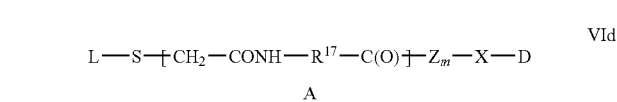

VId

Another illustrative Spacer unit A is that of Formula VId wherein $R^{17}$ is —$(CH_2)_5$—:

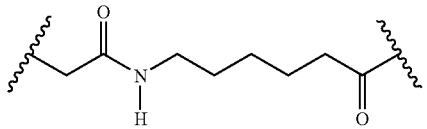

The spacer units of the invention expressly contemplate, but are not limited to conjugates prepared with cross-linker reagents: BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate), and including bis-maleimide reagents: DTME, BMB, BMDB, BMH, BMOE, BM(PEO)$_3$, and BM(PEO)$_4$, which are commercially available from Pierce Biotechnology, Inc., Customer Service Department, P.O. Box 117, Rockford, Ill. 61105 USA, 1-800-874-3723, International+815-968-0747. See pages 467-498, 2003-2004 of the Applications Handbook and Catalog. Bis-maleimide reagents allow the attachment of the thiol group of a cysteine residue of an antibody to a thiol-containing drug moiety, label, or linker intermediate, in a sequential or concurrent fashion. Other functional groups besides maleimide, which are reactive with a thiol group of an antibody, drug moiety, label, or linker intermediate include iodoacetamide, bromoacetamide, vinyl pyridine, disulfide, pyridyl disulfide, isocyanate, and isothiocyanate.

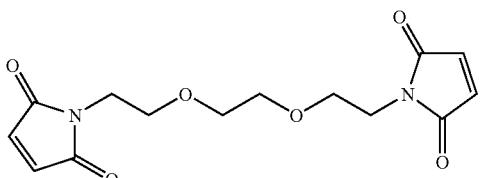

BM(PEO)$_3$

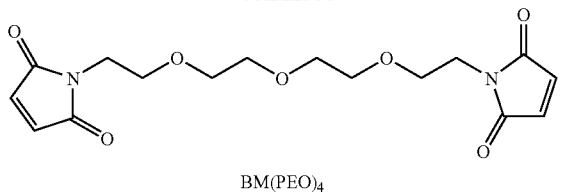

BM(PEO)₄

Useful spacer reagents can also be obtained via other commercial sources, such as Molecular Biosciences Inc.(Boulder, Colo.), or synthesized in accordance with procedures described in Toki et al (2002) J. Org. Chem. 67:1866-1872; U.S. Pat. No. 6,214,345 to Firestone et al; WO 02/088172; US 2003130189; US2003096743; WO 03/026577; WO 03/043583; and WO 04/032828.

Conjugates of the invention in which the spacer unit A is coupled to ligand L via an amide group may be prepared by reacting a free amine functional group on ligand L with an active ester containing precursor of spacer unit A. For example, a carboxyl group on spacer unit may be activated by reacting with N-hydroxysuccinimide and then reacted with L-NH₂ to form a conjugate in which L and A or coupled by way of an amide group.

Useful functional groups on an antibody for linking to the spacer unit, either naturally or via chemical manipulation include, but are not limited to, sulfhydryl (—SH), amino, hydroxyl, the anomeric hydroxyl group of a carbohydrate, and carboxyl. In one aspect, the reactive functional groups on the antibody are sulfhydryl and amino. Sulfhydryl groups can be generated by reduction of an intramolecular cysteine disulfide bond of an antibody. Alternatively, sulfhydryl groups can be generated by reaction of an amino group of a lysine moiety of an antibody using 2-iminothiolane (Traut's reagent) or another sulfhydryl generating reagent.

In another embodiment, the Spacer unit is linked to the Antibody unit via a disulfide bond between a sulfur atom of the Antibody unit and a sulfur atom of the Spacer unit. A representative Spacer unit of this embodiment is depicted within the square brackets of Formula VII, wherein Ab, $R^{17}$, Zm, X, D, and m are as defined above. The average number of drug moieties per antibody units is represented by p, which may be from 1 to about 8.

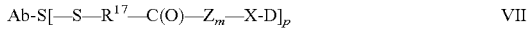

Ab-S[—S—$R^{17}$—C(O)—$Z_m$—X-D]$_p$        VII

In yet another embodiment, the reactive group of the Spacer contains a reactive site that can form a bond with a primary or secondary amino group of an antibody. Example of these reactive sites include, but are not limited to, activated esters such as succinimide esters, 4-nitrophenyl esters, pentafluorophenyl esters, tetrafluorophenyl esters, anhydrides, acid chlorides, sulfonyl chlorides, isocyanates and isothiocyanates. Representative Spacer units of this embodiment are depicted within the square brackets of Formulas VIIIa and VIIIb:

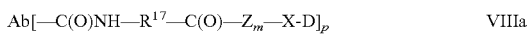

Ab[—C(O)NH—$R^{17}$—C(O)—$Z_m$—X-D]$_p$        VIIIa

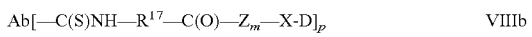

Ab[—C(S)NH—$R^{17}$—C(O)—$Z_m$—X-D]$_p$        VIIIb

In yet another embodiment, the reactive group of the Spacer reacts with an aldehyde, acetal, or ketal group on a sugar (carbohydrate) of a glycosylated antibody. For example, a carbohydrate can be mildly oxidized using a reagent such as sodium periodate and the resulting (—CHO) unit of the oxidized carbohydrate can be condensed with a Spacer that contains a functionality such as a hydrazide, an oxime, a primary or secondary amine, a hydrazine, a thiosemicarbazone, a hydrazine carboxylate, and an arylhydrazide such as those described by Kaneko, T. et al (1991) Bioconjugate Chem 2:133-41. Representative Spacer units of this embodiment are depicted within the square brackets of Formulas IXa, IXb, and IXc:

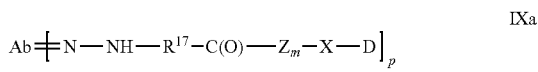

Ab—[N—NH—$R^{17}$-C(O)—$Z_m$-X—D]$_p$        IXa

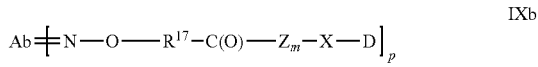

Ab—[N—O—$R^{17}$-C(O)—$Z_m$-X—D]$_p$        IXb

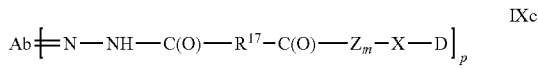

Ab—[N—NH—C(O)—$R^{17}$-C(O)—$Z_m$-X—D]$_p$        IXc

1. Drug Moiety (D)

The drug conjugates of the present invention are effective for the purposes for which the corresponding drugs are effective, and have superior efficacy and safety because of the ability, inherent in the ligand, to transport the drug to the desired cell where it is of particular benefit. Further, because the conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a protein such as tumor necrosis factor.

Exemplary drugs for use in the present invention are cytotoxic drugs, particularly those which are used for cancer therapy. Such drugs include, in general, DNA damaging agents, anti-metabolites, natural products and their analogs. Exemplary classes of cytotoxic agents include the enzyme inhibitors such as dihydrofolate reductase inhibitors, and thymidylate synthase inhibitors, DNA intercalators, DNA cleavers, topoisomerase inhibitors, the anthracycline family of drugs, the vinca drugs, the mitomycins, the bleomycins, the cytotoxic nucleosides, the pteridine family of drugs, diynenes, the podophyllotoxins, dolastatins, maytansinoids, differentiation inducers, and taxols. Particularly useful members of those classes include, for example, methotrexate, methopterin, dichloromethotrexate, 5-fluorouracil, 6-mercaptopurine, cytosine arabinoside, melphalan, leurosine, leurosideine, actinomycin, daunorubicin, doxorubicin, mitomycin C, mitomycin A, caminomycin, aminopterin, tallysomycin, podophyllotoxin and podophyllotoxin derivatives such as etoposide or etoposide phosphate, vinblastine, vincristine, vindesine, taxol, taxotere retinoic acid, butyric acid, N8-acetyl spermidine, camptothecin, calicheamicin, esperamicin, ene-diynes, and their analogues.

Exemplary drugs include the dolastatins and analogues thereof including: dolastatin A (U.S. Pat. No. 4,486,414), dolastatin B (U.S. Pat. No. 4,486,414), dolastatin 10 (U.S. Pat. Nos. 4,816,444, 5,410,024, 5,504,191, 5,521,284, 5,530, 097, 5,599,902, 5,635,483, 5,663,149, 5,665,860, 5,780,588, 6,034,065, 6,323,315), dolastatin 13 (U.S. Pat. No. 4,986, 988), dolastatin 14 (U.S. Pat. No. 5,138,036), dolastatin 15 (U.S. Pat. No. 4,879,278), dolastatin 16 (U.S. Pat. No. 6,239, 104), dolastatin 17 (U.S. Pat. No. 6,239,104) and dolastatin 18 (U.S. Pat. No. 6,239,104), each patent incorporated herein by reference in their entirety.

In exemplary embodiments of the invention, drug moiety D is a mitomycin, vinca alkaloid, taxol, anthracycline, a calicheamicin, maytansinoid or an auristatin.

It will be understood that chemical modifications may also be made to the desired compound in order to make reactions of that compound more convenient for purposes of preparing conjugates of the invention. For example a functional group e.g. amine, hydroxyl, or sulfhydryl, may be appended to the drug at a position which has minimal or an acceptable effect on the activity or other properties of the drug.

In the conjugate of Formula I, D is a drug moiety having pendant to the backbone thereof a chemically reactive functional group by means of which the drug backbone is bonded to the protein peptide linker, said functional group selected from the group consisting of a primary or secondary amine, hydroxyl, sulfhydryl or carboxyl.

Drugs containing an amine functional group for coupling to the self-immolative moiety include mitomycin-C, mitomycin-A, daunorubicin, doxorubicin, aminopterin, actinomycin, bleomycin, 9-amino camptothecin, N8-acetyl spermidine, 1-(2 chloroethyl)-1,2-dimethanesulfonyl hydrazide, tallysomycin, cytarabine, dolastatins (including auristatins) and derivatives thereof.

Drugs containing a hydroxyl functional group for coupling to the self-immolative moiety include etoposide, camptothecin, taxol, esperamicin, 1,8-dihydroxy-bicyclo[7.3.1] trideca-4-9-diene-2,6-diyne-13-one, (U.S. Pat. No. 5,198,560), podophyllotoxin, anguidine, vincristine, vinblastine, morpholine-doxorubicin, n-(5,5-diacetoxy-pentyl) doxorubicin, and derivatives thereof.

Drugs containing a sulfhydryl functional group for coupling to the self-immolative moiety include esperamicin and 6-mercaptopurine, and derivatives thereof.

Drugs containing one or more carboxyl functional groups for coupling to the self-immolative moiety include methotrexate, camptothecin (ring-opened form of the lactone), butyric acid, retinoic acid, and derivatives thereof.

Exemplary cytotoxic agents for use as drugs in the present invention include drugs of the following formulae:

The Mitomycin Group of Formula (1):

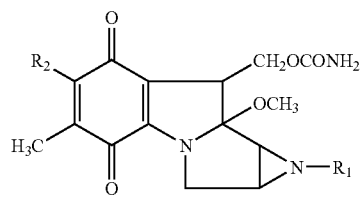

wherein $R_1$ is hydrogen or methyl; $R_2$ is —$NH_2$, —$OCH_3$, —$O(CH_2)_2$ OH, —$NH(CH_2)_2SS(CH_2)_2NHAc$, —NHCH=C=CH, —$NH(CH_2)_2SS(C_6H_4)NO_2$, —$O(CH_2)_2SS(CH_2)_2OH$, —N=CH—$NHOCH_3$, —$NH(C_6H_4)OH$, —$NH(CH_2)_2SS(CH_2)_2NHCO(CH_2)_2CH(NH_2)COOH$, and:

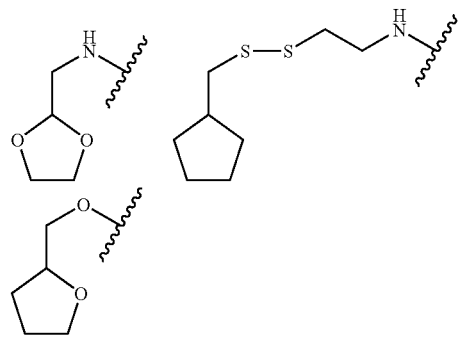

The Bleomycin Group of Formula (2):

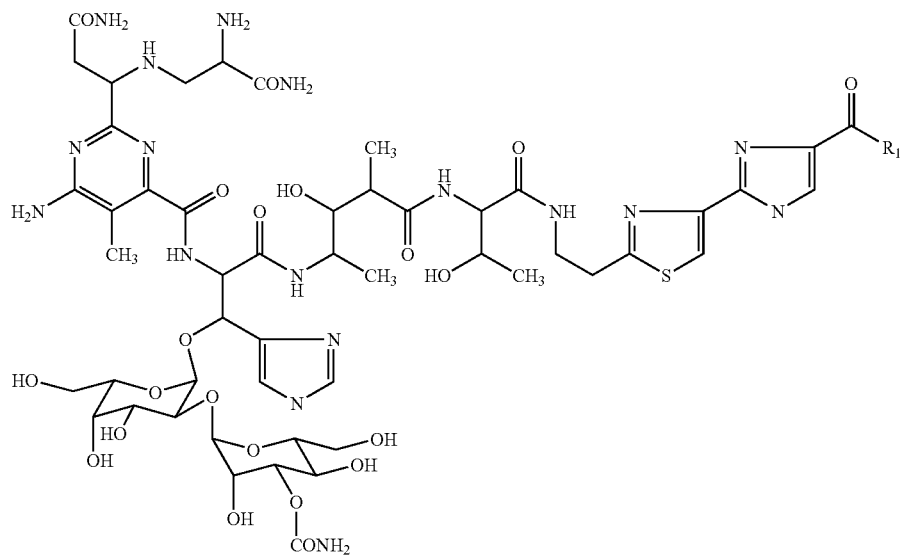

wherein $R_1$ is hydroxy, amino, $C_1$-$C_3$ alkylamino, di($C_1$-$C_3$alkyl)amino, $C_4$-$C_6$ polymethylene amino,

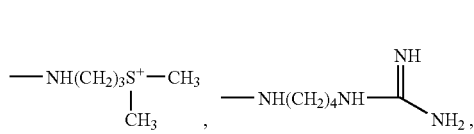

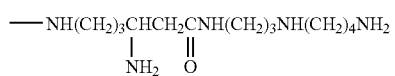

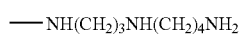

The Methotrexate Group of Formula (3):

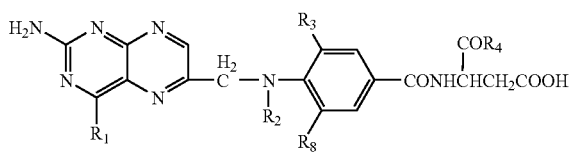

wherein $R_1$ is amino or hydroxy; $R_2$ is hydrogen or methyl; $R_3$ is hydrogen, fluoro, chloro, bromo or iodo; $R_4$ is hydroxy or a moiety which completes a salt of the carboxylic acid.

Melphalan of Formula (4):

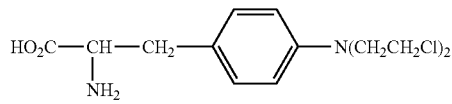

Mercaptopurine of Formula (5):

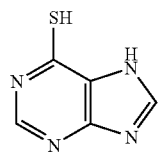

A Cytosine Arabinoside of Formula (6):

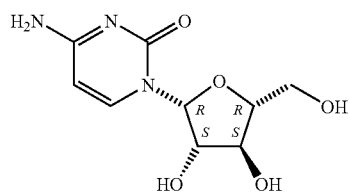

The Podophyllotoxins of Formula (7):

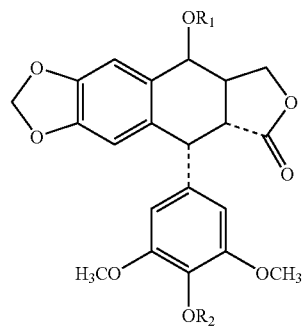

wherein $R_2$ is hydrogen, $R_1$ is hydrogen or

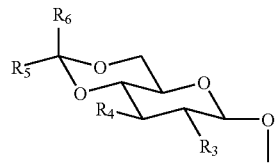

wherein $R_3$ is $NH_2$, OH, $OCH_3$, NH($C_1$-$C_3$ alkyl) or N($C_1$-$C_3$ alkyl)$_2$; $R_4$ is OH, or $NH_2$; $R_5$ is methyl or thienyl, and $R_6$ is hydrogen or methyl, or a phosphate salt thereof.

The Vinca Alkaloid Group of Drugs of Formula (8):

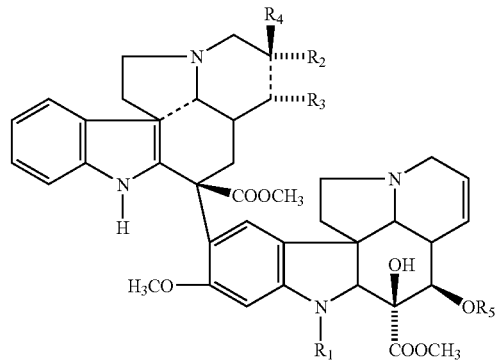

wherein $R_1$ is H, $CH_3$ or CHO;
when $R_2$ and $R_3$ are taken singly, $R_3$ is H, and one of $R_4$ and $R_2$ is ethyl and the other is H or OH; when $R_2$ and $R_3$ are taken together with the carbons to which they are attached, they form an oxirane ring in which case $R_4$ is ethyl; $R_5$ is hydrogen, ($C_1$-$C_3$ alkyl)-CO, or chlorosubstituted ($C_1$-$C_3$ alkyl)-CO. As used herein "$C_1$-$C_3$ alkyl" means a straight or branched carbon chain having from one to three carbon atoms; examples include methyl, ethyl, n-propyl and isopropyl.

Difluoronucleosides of Formula (9):

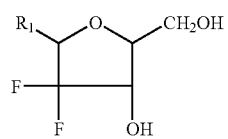

in which $R_1$ is a base of one of the formulae:

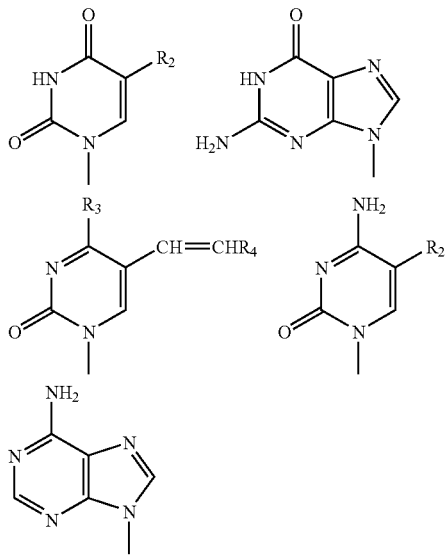

wherein $R_2$ is hydrogen, methyl, bromo, fluoro, chloro, or iodo; $R_3$ is —OH or —NH$_2$; $R_4$ is hydrogen, bromo, chloro, or iodo.

Taxols of Formula (10):

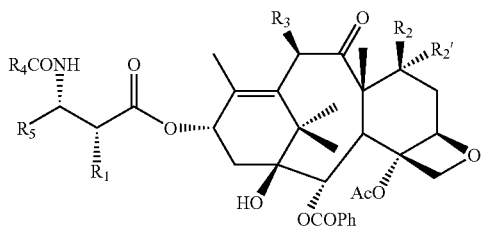

wherein $R_1$ is hydroxy; $R_2$ is hydrogen, hydroxy or fluoro; $R_3$ is hydrogen, hydroxy, or acetoxy; $R_4$ is aryl, substituted aryl, $C_{1-6}$ alkyl, $C_{2-6}$ alkenyl, $C_{2-6}$ alkynyl or t-butoxy; $R_5$ is $C_{1-6}$ alkyl, $C_{2-6}$ alkenyl, $C_{2-6}$ alkynyl, or -Z-$R_6$; Z is a direct bond, $C_{1-6}$ alkyl or $C_{2-6}$ alkenyl; $R_6$ is aryl, substituted aryl, $C_{3-6}$ cycloalkyl, thienyl or furyl.

Anguidines of Formula (11):

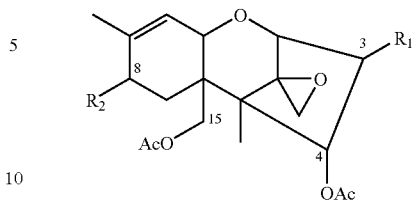

wherein $R_1$ is OH or O; and $R_2$ is H or O. Anguidine can be targeted at the C-3, C-4, C-8 or C-15 positions, as an ester or hydrazone.

The Anthracycline Antibiotics of Formula (12):

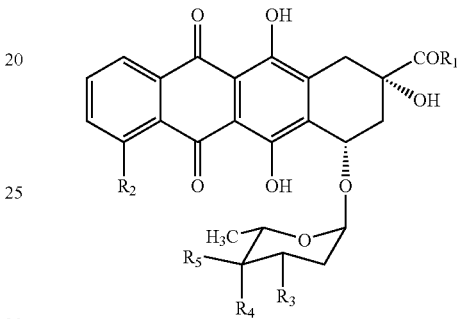

wherein $R_1$ is —CH$_3$, —CH$_2$OH, —CH$_2$OCO(CH$_2$)$_3$CH$_3$ or —CH$_2$OCOCH(OC2H$_5$)$_2$; $R_2$ is —OCH$_3$, —OH or —H; $R_3$ is —NH$_2$, —NHCOCF$_3$, 4-morpholinyl, 3-cyano-4-morpholinyl, 1-piperidinyl, 4-methoxy-1-piperidinyl, benzylamine, dibenzylamine, cyanomethylamine, 1-cyano-2-methoxyethyl amine, or NH—(CH$_2$)$_4$—CH(OAc)$_2$; $R_4$ is —OH, —OTHP, or —H; and $R_5$ is —OH or —H provided that $R_5$ is not —OH when $R_4$ is —OH or —OTHP.

It is appreciated that the above structures and descriptions include compounds which are drugs, or are derivatives of drugs, and which have acquired in the art different generic, trade, or trivial names.

Table I, which follows, represents a number of anthracycline drugs and their generic or trivial names and which are exemplary for use in the present invention. Doxorubicin, shown in Table I, (also referred to herein as "DOX") is the anthracycline of Formula (12) in which $R_1$ is —CH$_2$OH, $R_2$ is —OCH$_3$, $R_3$ is —NH$_2$, $R_4$ is —OH, and $R_5$ is —H.

TABLE I

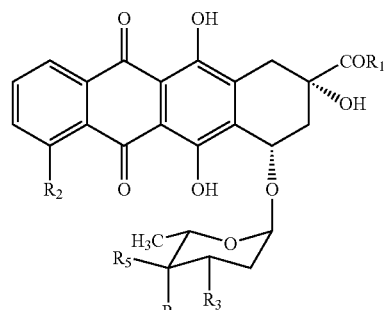

| Compound | $R_1$ | $R_2$ | $R_3$ | $R_4$ | $R_5$ |
|---|---|---|---|---|---|
| Daunorubicin | CH$_3$ | OCH$_3$ | NH$_2$ | OH | H |
| Doxorubicin | CH$_2$OH | OCH$_3$ | NH$_2$ | OH | H |

TABLE I-continued

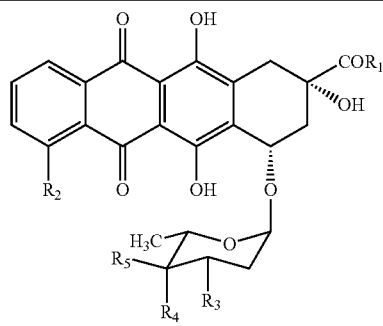

| Compound | $R_1$ | $R_2$ | $R_3$ | $R_4$ | $R_5$ |
|---|---|---|---|---|---|
| Detorubicin | $CH_2OCOCH(OC_2H_5)_2$ | $OCH_3$ | $NH_2$ | OH | H |
| Carminomycin | $CH_3$ | OH | $NH_2$ | OH | H |
| Idarubicin | $CH_3$ | H | $NH_2$ | OH | H |
| Epirubicin | $CH_2OH$ | $OCH_3$ | $NH_2$ | H | OH |
| Esorubicin | $CH_2OH$ | $OCH_3$ | $NH_2$ | H | H |
| THP | $CH_2OH$ | $OCH_3$ | $NH_2$ | OTHP | H |
| AD-32 | $CH_2OCO(CH_2)_3CH_3$ | $OCH_3$ | $NHCOCF_3$ | OH | H |
| Morpholino-Dox | $CH_2OH$ | $OCH_3$ | morpholin-4-yl | OH | H |
| Cyano-Morpholino-Dox | $CH_2OH$ | $OCH_3$ | 3-cyanomorpholin-4-yl | OH | H |
| DAPDox | $CH_2OH$ | $OCH_3$ | $NH(CH_2)_4CH(OAc)_2$ | OH | H |

Auristatins of Formula (13):

The drug moiety (D) of the conjugates of Formula I include dolastatins and their peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Embodiments of drug moiety (D) of the antibody-drug conjugates (ADC) of Formula I include the N-terminus linked monomethylauristatin drug moieties $D_E$ and $D_F$, disclosed in Senter et al, Proceedings of the American Association for Cancer Research, Volume 45, Abstract Number 623, presented Mar. 28, 2004, and having the structures:

wherein the wavy line of $D_E$ and $D_E$ indicates the covalent attachment site to A, W, or Y of the Linker, and independently at each location:

$R^2$ is selected from H and $C_1$-$C_8$ alkyl;

$R^3$ is selected from H, $C_1$-$C_8$ alkyl, $C_3$-$C_8$ carbocycle, aryl, $C_1$-$C_8$ alkyl-($C_6$-$C_{20}$ aryl), $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, $C_6$-$C_{20}$ aryl, $C_1$-$C_8$ alkyl-($C_6$-$C_{20}$ aryl), $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$D_E$

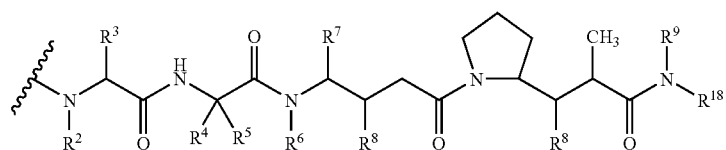

$D_F$

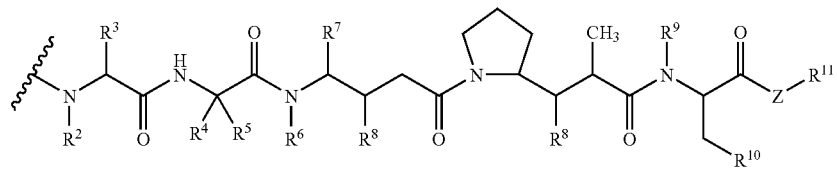

$R^7$ is selected from H, $C_1$-$C_8$ alkyl, $C_3$-$C_8$ carbocycle, $C_6$-$C_{20}$ aryl, $C_1$-$C_8$ alkyl-($C_6$-$C_{20}$ aryl), $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{10}$ is selected from $C_6$-$C_{20}$ aryl or $C_3$-$C_8$ heterocycle;

Z is O, S, NH, or $NR^{12}$, wherein $R^{12}$ is $C_1$-$C_8$ alkyl;

$R^{11}$ is selected from H, $C_1$-$C_{20}$ alkyl, aryl, $C_3$-$C_8$ heterocycle, —($R^{13}O)_m$—$R^{14}$, or —($R^{13}O)_m$, —$CH(R^{15})_2$;

m is an integer ranging from 1-1000;

$R^{13}$ is $C_2$-$C_8$ alkyl;

$R^{14}$ is H or $C_1$-$C_8$ alkyl;

each occurrence of $R^{15}$ is independently H, COOH, —$(CH_2)_n$—$N(R^{16})_2$, —$(CH_2)_n$—$SO_3H$, or —$(CH_2)_n$—$SO_3$—$C_1$-$C_8$ alkyl;

each occurrence of $R^{16}$ is independently H, $C_1$-$C_8$ alkyl, or —$(CH_2)_n$—COOH;

$R^{18}$ is selected from —$C(R^8)_2$—$C(R^8)_2$—($C_6$-$C_{20}$ aryl), —$C(R^8)_2$—$C(R^8)_2$—($C_3$-$C_8$ heterocycle), and —$C(R^8)_2$—$C(R^8)_2$—($C_3$-$C_8$ carbocycle); and n is an integer ranging from 0 to 6.

Exemplary embodiments of $R^{11}$ include:

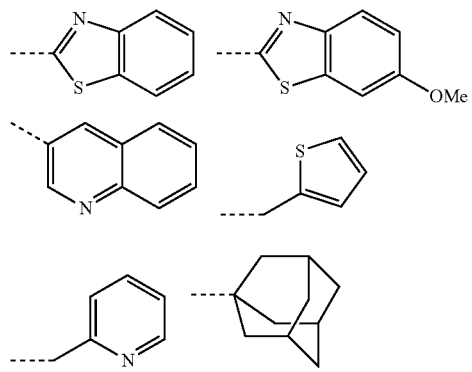

An exemplary embodiment of drug moiety $D_E$ is MMAE:

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry. The auristatin/dolastatin drug moieties may be prepared according to the methods of: U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. *Synthesis*, 1996, 719-725; and Pettit et al (1996) J. Chem. Soc. Perkin Trans. 1 5:859-863.

Calicheamicin, Ene-Diyne Derivatives (14):

Another useful class of drug moiety for Formula IV compounds is the ene-diyne family of calicheamicins (U.S. Pat. Nos. 5,053,394; 4,970,198; 5,079,233; 5,773,001; 5,606,040; 5,739,116; 5,264,586; 5,384,412) and esperamicins (U.S. Pat. No. 5,877,296).

Maytansinoid Derivatives of Formula (15):

The drug moiety (D) of the conjugates of Formula IV include maytansinoids having the structure:

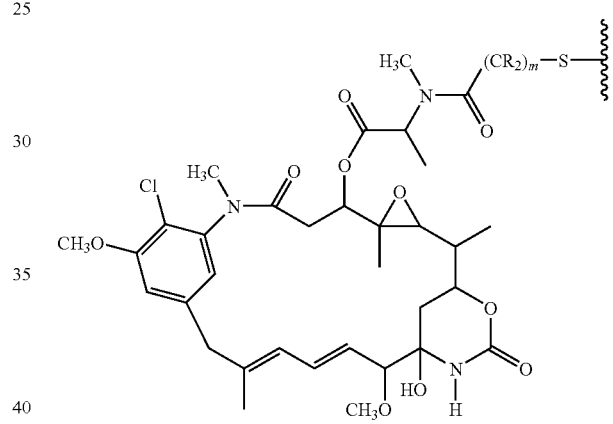

where the wavy line indicates the covalent attachment of the sulfur atom of D to a linker (L) of a Formula IV compound, such as an antibody drug conjugate (ADC). R may indepen-

MMAE

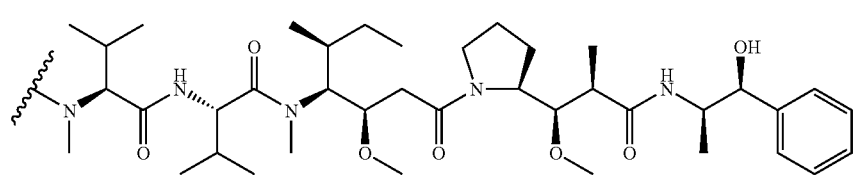

An exemplary embodiment of drug moiety $D_F$ is MMAF:

MMAF

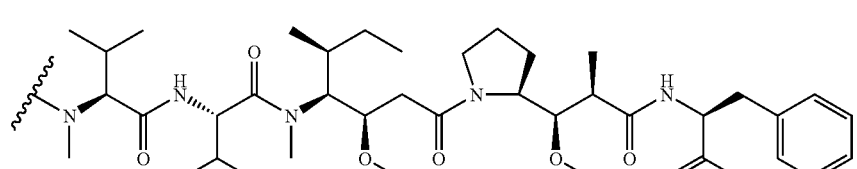

dently be H or a $C_1$-$C_6$ alkyl. The alkylene chain attaching the amide group to the sulfur atom may be methanyl, ethanyl, or propyl, i.e. m is 1, 2, or 3.

Maytansine compounds inhibit cell proliferation by inhibiting the formation of microtubules during mitosis through inhibition of polymerization of the microtubulin protein, tubulin (Remillard et al (1975) Science 189:1002-1005; U.S. Pat. No. 5,208,020). Maytansine was isolated from the east African shrub *Maytenus serrata* and shown to be 100- to 1000-fold more cytotoxic than conventional cancer chemotherapeutic agents like methotrexate, daunorubicin, and vincristine (U.S. Pat. No. 3,896,111). Subsequently, it was discovered that some microbes also produce maytansinoids, such as maytansinol and C-3 esters of maytansinol (U.S. Pat. No. 4,151,042). Synthetic C-3 esters of maytansinol and analogues of maytansinol have also been reported (Kupchan et al., (1978) J. Med. Chem. 21:31-37; Higashide et al. (1977) Nature 270:721-722; Kawai et al., 32 Chem. Pharm. (1984) Bull. 3441-3451). Analogs of maytansinol from which C-3 esters have been prepared include maytansinol with modifications on the aromatic ring (e.g. dechloro) or at the C-9, C-14 (e.g. hydroxylated methyl group), C-15, C-18, C-20 and C-4, 5. The naturally occurring and synthetic C-3 esters can be classified into two groups:

(a) C-3 esters with simple carboxylic acids (U.S. Pat. Nos. 4,248,870; 4,265,814; 4,308,268; 4,308,269; 4,309,428; 4,317,821; 4,322,348; and 4331598), and (b) C-3 esters with derivatives of N-methyl-L-alanine (U.S. Pat. Nos. 4,137,230 and 4,260,608; and Kawai et al., (1984) Chem. Pharm. Bull. 32:3441-3451). Esters of group (b) were found to be much more cytotoxic than esters of group (a).

As with other drug moieties, all stereoisomers of the maytansinoid drug moiety are contemplated for the compounds of the invention, i.e. any combination of R and S configurations at the chiral carbons of D. In one embodiment, the maytansinoid drug moiety (D) will have the following stereochemistry:

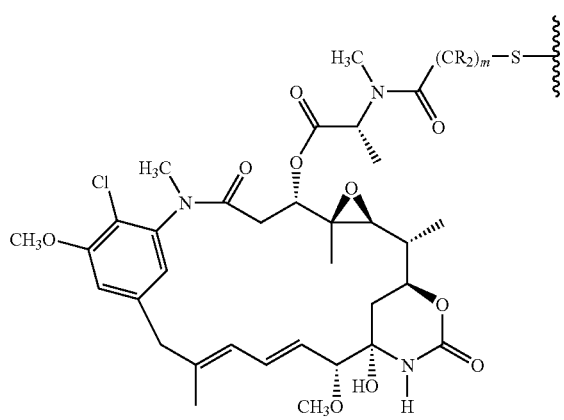

Exemplary embodiments of maytansinoid drug moieties include: DM1, $(CR_2)_m=CH_2CH_2$; DM3, $(CR_2)_m=CH_2CH_2CH(CH_3)$; and DM4, $(CR_2)_m=CH_2CH_2C(CH_3)_2$, having the structures:

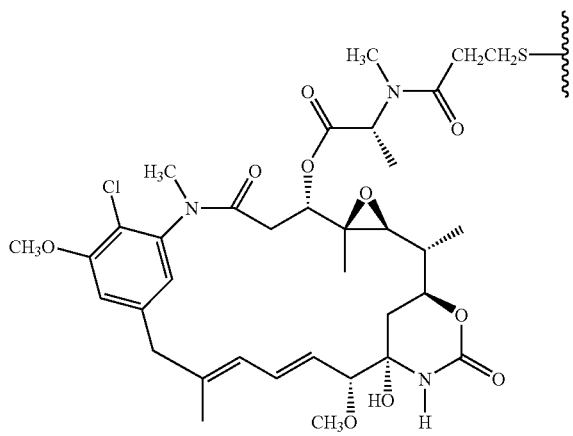

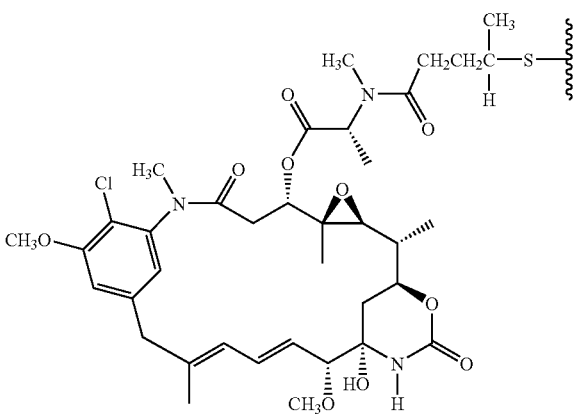

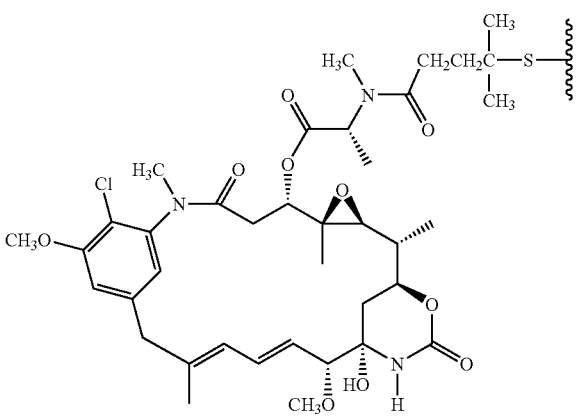

1. Ligand (L)

The "ligand" moiety L includes within its scope any molecule that specifically binds or reactively associates or complexes with a receptor or other receptive moiety associated with a given target cell population. This cell reactive molecule is coupled to a the linker moiety of the conjugate by way of a free reactive sulfhydryl (—SH), amine (—$NH_2$), aldehyde (—CHO) or carboxyl (—COOH) group or can be modified to contain such a sulfhydryl, amine, aldehyde or carboxyl group. The ligand L acts to deliver the therapeutically active drug moiety D to the particular target cell population with which the ligand reacts and may be internalized by such cells wherein it is exposed to an enzyme for release of the active drug. Such ligand molecules include, but are not limited to, large molecular weight proteins such as, for example, antibodies, smaller molecular weight proteins, polypeptide or peptide ligands, and non-peptidyl ligands.

Useful non-immunoreactive protein, polypeptide, or peptide antibodies which comprise L in Formula IV antibody-drug conjugates (ADC) include, but are not limited to, transferrin, epidermal growth factors ("EGF"), bombesin, gastrin, gastrin-releasing peptide, platelet-derived growth factor, IL-2, IL-6, transforming growth factors ("TGF"), such as TGF-α and TGF-β, vaccinia growth factor ("VGF"), insulin and insulin-like growth factors I and II, lectins and apoprotein from low density lipoprotein.

Antibodies

Where ligand L of Formula IV is an antibody, the antibody unit (Ab-) includes within its scope any unit of an antibody (Ab) that binds or reactively associates or complexes with a receptor, antigen or other receptive moiety associated with a given target-cell population. An antibody can be any protein or protein-like molecule that binds to, complexes with, or reacts with a moiety of a cell population sought to be therapeutically or otherwise biologically modified. In one aspect, the antibody unit acts to deliver the Drug moiety to the particular target cell population with which the antibody unit reacts. Such antibodies include, but are not limited to, large molecular weight proteins such as, full-length antibodies and antibody fragments.

Antibodies which comprise L in Formula IV antibody-drug conjugates (ADC) and which may be useful in the treatment of cancer include, but are not limited to, antibodies against tumor-associated antigens (TAA). Such tumor-associated antigens are known in the art, and can prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Examples of TAA include, but are not limited to, TAA (1)-(35) listed below. For convenience, information relating to these antigens, all of which are known in the art, is listed below and includes names, alternative names, Genbank accession numbers and primary reference(s). Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

Tumor-Associated Antigens (1)-(35):

(1) BMPR1B (bone morphogenetic protein receptor-type IB, Genbank accession no. NM_001203)

ten Dijke, P., et al Science 264 (5155):101-104 (1994), Oncogene 14 (11):1377-1382 (1997)); WO2004063362 (Claim 2); WO2003042661 (Claim 12); US2003134790-A1 (Page 38-39); WO2002102235 (Claim 13; Page 296); WO2003055443 (Page 91-92); WO200299122 (Example 2; Page 528-530); WO2003029421 (Claim 6); WO2003024392 (Claim 2; FIG. 112); WO200298358 (Claim 1; Page 183); WO200254940 (Page 100-101); WO200259377(Page 349-350); WO200230268 (Claim 27; Page 376); WO200148204 (Example; FIG. 4) NP_001194 bone morphogenetic protein receptor, type IB /pid=NP_001194.1

Cross-references: MIM:603248; NP_001194.1; NM_001203_1

(2) E16 (LAT1, SLC7A5, Genbank accession no. NM_003486) Biochem. Biophys. Res. Commun 255 (2), 283-288 (1999), Nature 395 (6699):288-291 (1998), Gaugitsch, H. W., et al (1992) J. Biol. Chem. 267 (16):11267-11273); WO2004048938 (Example 2); WO2004032842 (Example IV); WO2003042661 (Claim 12); WO2003016475 (Claim 1); WO200278524 (Example 2); WO200299074 (Claim 19; Page 127-129); WO200286443 (Claim 27; Pages 222, 393); WO2003003906 (Claim 10; Page 293); WO200264798 (Claim 33; Page 93-95); WO200014228 (Claim 5; Page 133-136); US2003224454 (FIG. 3); WO2003025138 (Claim 12; Page 150);

NP_003477 solute carrier family 7 (cationic amino acid transporter, y+ system), member 5/pid=NP_003477.3—*Homo sapiens*

Cross-references: MIM:600182; NP_003477.3; NM_015923; NM_003486_1

(3) STEAP1 (six transmembrane epithelial antigen of prostate, Genbank accession no. NM_012449)

Figure 2:
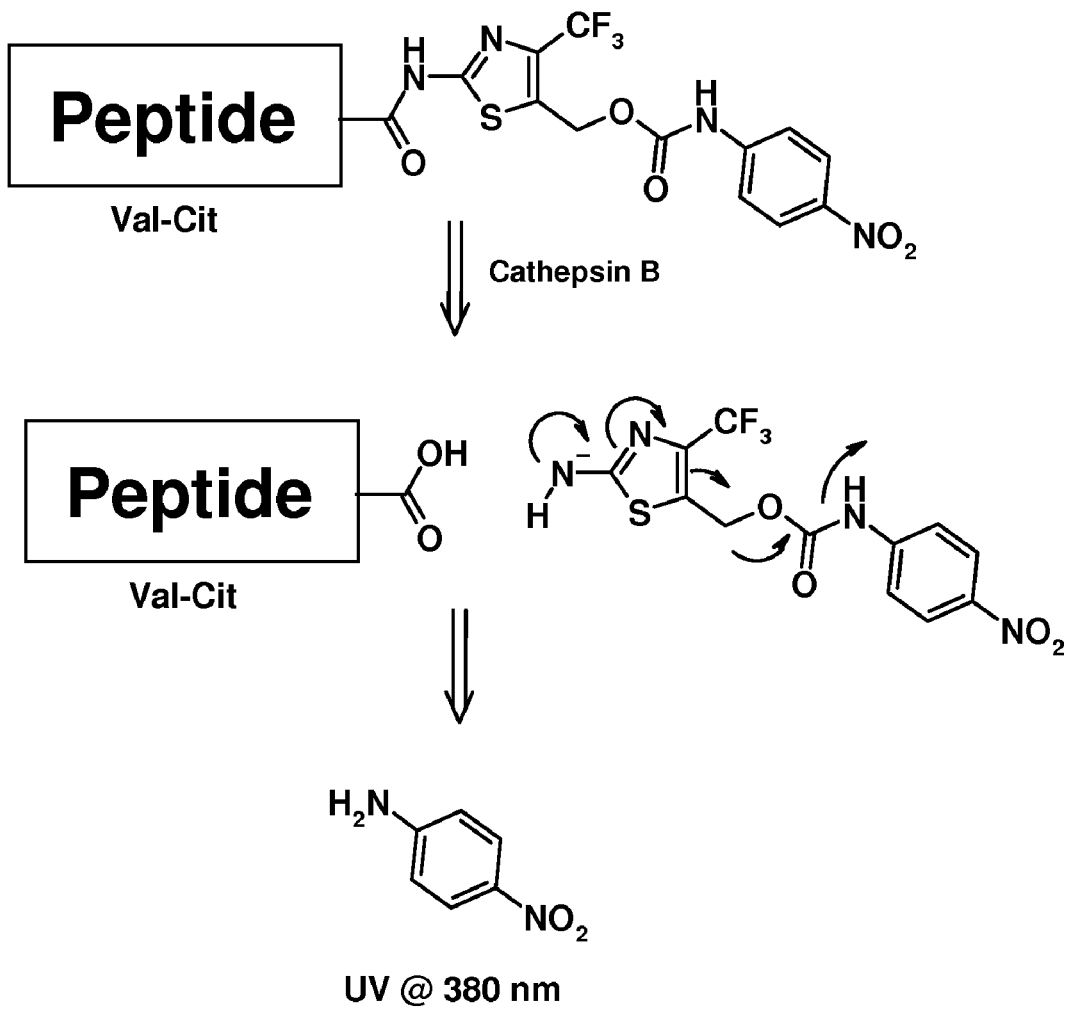
FIG. 2 is a schematic diagram illustrating the cleavage of a thiazole-containing self-immolative moiety by cathepsin B.

Cancer Res. 61 (15), 5857-5860 (2001), Hubert, R. S., et al (1999) Proc. Natl. Acad. Sci. U.S.A. 96 (25):14523-14528); WO2004065577 (Claim 6); WO2004027049 (FIG. 1L); EP1394274 (Example 11); WO2004016225 (Claim 2); WO2003042661 (Claim 12); US2003157089 (Example 5); US2003185830 (Example 5); US2003064397 (FIG. 2); WO200289747 (Example 5; Page 618-619); WO2003022995 (Example 9; FIG. 13A, Example 53; Page 173, Example 2; FIG. 2A);

NP_036581 six transmembrane epithelial antigen of the prostate

Cross-references: MIM:604415; NP_036581.1; NM_012449_1

(4) 0772P(CA125, MUC16, Genbank accession no. AF361486) J. Biol. Chem. 276 (29):27371-27375 (2001)); WO2004045553 (Claim 14); WO200292836 (Claim 6; FIG. 12); WO200283866 (Claim 15; Page 116-121); US2003124140 (Example 16); US2003091580 (Claim 6); WO200206317 (Claim 6; Page 400-408);

Cross-references: GI:34501467; AAK74120.3; AF361486_1

(5) MPF (MPF, MSLN, SMR, megakaryocyte potentiating factor, mesothelin, Genbank accession no. NM_005823)

Yamaguchi, N., et al Biol. Chem. 269 (2), 805-808 (1994), Proc. Natl. Acad. Sci. U.S.A. 96 (20):11531-11536 (1999), Proc. Natl. Acad. Sci. U.S.A. 93 (1):136-140 (1996), J. Biol. Chem. 270 (37):21984-21990 (1995)); WO2003101283 (Claim 14); (WO2002102235 (Claim 13; Page 287-288); WO2002101075 (Claim 4; Page 308-309); WO200271928 (Page 320-321); WO9410312 (Page 52-57);

Cross-references: MIM:601051; NP_005814.2; NM_005823_1

(6) Napi3b (NAPI-3B, NPTIIb, SLC34A2, solute carrier family 34 (sodium phosphate), member 2, type II sodiumdependent phosphate transporter 3b, Genbank accession no. NM_006424)

J. Biol. Chem. 277 (22):19665-19672 (2002), Genomics 62 (2):281-284 (1999), Feild, J. A., et al (1999) Biochem. Biophys. Res. Commun. 258 (3):578-582); WO2004022778 (Claim 2); EP1394274 (Example 11); WO2002102235 (Claim 13; Page 326); EP875569 (Claim 1; Page 17-19); WO200157188 (Claim 20; Page 329); WO2004032842 (Example IV); WO200175177 (Claim 24; Page 139-140);

Cross-references: MIM:604217; NP_006415.1; NM_006424_1

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878)

Nagase T., et al (2000) DNA Res. 7 (2):143-150); WO2004000997 (Claim 1); WO2003003984 (Claim 1); WO200206339 (Claim 1; Page 50); WO200188133 (Claim 1; Page 41-43, 48-58); WO2003054152 (Claim 20); WO2003101400 (Claim 11);

Accession: □9P283; EMBL; AB040878; BAA95969.1. Genew; HGNC:10737;

(8) PSCA hlg (2700050C12Rik, C530008O16Rik, RIKEN cDNA 2700050C12, RIKEN cDNA 2700050C12 gene, Genbank accession no. AY358628); US2003129192 (Claim 2); US2004044180 (Claim 12); US2004044179 (Claim 11); US2003096961 (Claim 11); US2003232056 (Example 5); WO2003105758 (Claim 12); US2003206918 (Example 5); EP1347046 (Claim 1); WO2003025148 (Claim 20);

Cross-references: GI:37182378; AAQ88991.1; AY358628_1

(9) ETBR (Endothelin type B receptor, Genbank accession no. AY275463);

Nakamuta M., et al Biochem. Biophys. Res. Commun. 177, 34-39, 1991; Ogawa Y., et al Biochem. Biophys. Res. Commun. 178, 248-255, 1991; Arai H., et al Jpn. Circ. J. 56, 1303-1307, 1992; Arai H., et al J. Biol. Chem. 268, 3463-3470, 1993; Sakamoto A., Yanagisawa M., et al Biochem. Biophys. Res. Commun. 178, 656-663, 1991; Elshourbagy N. A., et al J. Biol. Chem. 268, 3873-3879, 1993; Haendler B., et al J. Cardiovasc. Pharmacol. 20, s1-S4, 1992; Tsutsumi M., et al Gene 228, 43-49, 1999; Strausberg R. L., et al Proc. Natl. Acad. Sci. U.S.A. 99, 16899-16903, 2002; Bourgeois C., et al J. Clin. Endocrinol. Metab. 82, 3116-3123, 1997; Okamoto Y., et al Biol. Chem. 272, 21589-21596, 1997; Verheij J. B., et al Am. J. Med. Genet. 108, 223-225, 2002; Hofstra R. M. W., et al Eur. J. Hum. Genet. 5, 180-185, 1997; Puffenberger E. G., et al Cell 79, 1257-1266, 1994; Attie T., et al, Hum. Mol. Genet. 4, 2407-2409, 1995; Auricchio A., et al Hum. Mol. Genet. 5:351-354, 1996; Amiel J., et al Hum. Mol. Genet. 5, 355-357, 1996; Hofstra R. M. W., et al Nat. Genet. 12, 445-447, 1996; Svensson P. J., et al Hum. Genet. 103, 145-148, 1998; Fuchs S., et al Mol. Med. 7, 115-124, 2001; Pingault V., et al (2002) Hum. Genet. 111, 198-206; WO2004045516 (Claim 1); WO2004048938 (Example 2); WO2004040000 (Claim 151); WO2003087768 (Claim 1); WO2003016475 (Claim 1); WO2003016475 (Claim 1); WO200261087 (FIG. 1); WO2003016494 (FIG. 6); WO2003025138 (Claim 12; Page 144); WO200198351 (Claim 1; Page 124-125); EP522868 (Claim 8; FIG. 2); WO200177172 (Claim 1; Page 297-299); US2003109676; U.S. Pat. No. 6,518,404 (FIG. 3); U.S. Pat. No. 5,773,223 (Claim 1a; Col 31-34); WO2004001004;

(10) MSG783 (RNF124, hypothetical protein FLJ20315, Genbank accession no. NM_017763); WO2003104275 (Claim 1); WO2004046342 (Example 2); WO2003042661 (Claim 12); WO2003083074 (Claim 14; Page 61); WO2003018621 (Claim 1); WO2003024392 (Claim 2; FIG. 93); WO200166689 (Example 6);

Cross-references: LocusID:54894; NP_060233.2; NM_017763_1

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138)

Lab. Invest. 82 (11):1573-1582 (2002)); WO2003087306; US2003064397 (Claim 1; FIG. 1); WO200272596 (Claim 13; Page 54-55); WO200172962 (Claim 1; FIG. 4B); WO2003104270 (Claim 11); WO2003104270 (Claim 16); US2004005598 (Claim 22); WO2003042661 (Claim 12); US2003060612 (Claim 12; FIG. 10); WO200226822 (Claim 23; FIG. 2); WO200216429 (Claim 12; FIG. 10);

Cross-references: GI:22655488; AAN04080.1; AF455138_1

(12) TrpM4 (BR22450, FLJ20041, TRPM4, TRPM4B, transient receptor potential cation channel, subfamily M, member 4, Genbank accession no. NM_017636) Xu, X. Z., et al Proc. Natl. Acad. Sci. U.S.A. 98 (19):10692-10697 (2001), Cell 109 (3):397-407 (2002), J. Biol. Chem. 278 (33):30813-30820 (2003)); US2003143557 (Claim 4); WO200040614 (Claim 14; Page 100-103); WO200210382 (Claim 1; FIG. 9A); WO2003042661 (Claim 12); WO200230268 (Claim 27; Page 391); US2003219806 (Claim 4); WO200162794 (Claim 14; FIG. 1A-D);

Cross-references: MIM:606936; NP_060106.2; NM_017636_1

(13) CRIPTO (CR, CR1, CRGF, CRIPTO, TDGF1, teratocarcinoma-derived growth factor, Genbank accession no. NP_003203 or NM_003212) Ciccodicola, A., et al EMBO J. 8 (7):1987-1991 (1989), Am. J. Hum. Genet. 49 (3):555-565 (1991)); US2003224411 (Claim 1); WO2003083041 (Example 1); WO2003034984 (Claim 12); WO200288170 (Claim 2; Page 52-53); WO2003024392 (Claim 2; FIG. 58); WO200216413 (Claim 1; Page 94-95, 105); WO200222808 (Claim 2; FIG. 1); U.S. Pat. No. 5,854,399 (Example 2; Col 17-18); U.S. Pat. No. 5,792,616 (FIG. 2);

Cross-references: MIM:187395; NP_003203.1; NM_003212_1

(14) CD21 (CR2 (Complement receptor 2) or C3DR(C3d/Epstein Barr virus receptor) or Hs.73792 Genbank accession no. M26004)

Fujisaku et al (1989) J. Biol. Chem. 264 (4):2118-2125); Weis J. J., et al J. Exp. Med. 167, 1047-1066, 1988; Moore M., et al Proc. Natl. Acad. Sci. U.S.A. 84, 9194-9198, 1987; Barel M., et al Mol. Immunol. 35, 1025-1031, 1998; Weis J. J., et al Proc. Natl. Acad. Sci. U.S.A. 83, 5639-5643, 1986; Sinha S. K., et al (1993) J. Immunol. 150, 5311-5320; WO2004045520 (Example 4); US2004005538 (Example 1); WO2003062401 (Claim 9); WO2004045520 (Example 4); WO9102536 (FIG. 9.1-9.9); WO2004020595 (Claim 1);

Accession: P20023; Q13866; Q14212; EMBL; M26004; AAA35786.1.

(15) CD79b (CD79B, CD79β, IGb (immunoglobulin-associated beta), B29, Genbank accession no. NM_000626 or 11038674)

Proc. Natl. Acad. Sci. U.S.A. (2003) 100 (7):4126-4131, Blood (2002) 100 (9):3068-3076, Muller et al (1992) Eur. J. Immunol. 22 (6):1621-1625); WO2004016225 (Claim 2, FIG. 140); WO2003087768, US2004101874 (Claim 1, page 102); WO2003062401 (Claim 9); WO200278524 (Example 2); US2002150573 (Claim 5, page 15); U.S. Pat. No. 5,644, 033; WO2003048202 (Claim 1, pages 306 and 309); WO 99/558658, U.S. Pat. No. 6,534,482 (Claim 13, FIG. 17A/B); WO200055351 (Claim 11, pages 1145-1146);
  Cross-references: MIM:147245; NP_000617.1; NM_000626_1
(16) FcRH2 (IFGP4, IRTA4, SPAP1A (SH2 domain containing phosphatase anchor protein 1a), SPAP1B, SPAP1C, Genbank accession no. NM_030764) Genome Res. 13 (10):2265-2270 (2003), Immunogenetics 54 (2):87-95 (2002), Blood 99 (8):2662-2669 (2002), Proc. Natl. Acad. Sci. U.S.A. 98 (17):9772-9777 (2001), Xu, M. J., et al (2001) Biochem. Biophys. Res. Commun 280 (3):768-775; WO2004016225 (Claim 2); WO2003077836; WO200138490 (Claim 5; FIG. 18D-1-18D-2); WO2003097803 (Claim 12); WO2003089624 (Claim 25);
  Cross-references: MIM:606509; NP_110391.2; NM_030764_1
(17) HER2 (ErbB2, Genbank accession no. M11730) Coussens L., et al Science (1985) 230(4730):1132-1139); Yamamoto T., et al Nature 319, 230-234, 1986; Semba K., et al Proc. Natl. Acad. Sci. U.S.A. 82, 6497-6501, 1985; Swiercz J. M., et al J. Cell Biol. 165, 869-880, 2004; Kuhns J. J., et al J. Biol. Chem. 274, 36422-36427, 1999; Cho H.-S., et al Nature 421, 756-760, 2003; Ehsani A., et al (1993) Genomics 15, 426-429; WO2004048938 (Example 2); WO2004027049 (FIG. 1I); WO2004009622; WO2003081210; WO2003089904 (Claim 9); WO2003016475 (Claim 1); US2003118592; WO2003008537 (Claim 1); WO2003055439 (Claim 29; FIG. 1A-B); WO2003025228 (Claim 37; FIG. 5C); WO200222636 (Example 13; Page 95-107); WO200212341 (Claim 68; FIG. 7); WO200213847 (Page 71-74); WO200214503 (Page 114-117); WO200153463 (Claim 2; Page 41-46); WO200141787 (Page 15); WO200044899 (Claim 52; FIG. 7); WO200020579 (Claim 3; FIG. 2); U.S. Pat. No. 5,869,445 (Claim 3; Col 31-38); WO9630514 (Claim 2; Page 56-61); EP1439393 (Claim 7); WO2004043361 (Claim 7); WO2004022709; WO200100244 (Example 3; FIG. 4);
  Accession: P04626; EMBL; M11767; AAA35808.1. EMBL; M11761; AAA35808.1.
(18) NCA (CEACAM6, Genbank accession no. M18728); Barnett T., et al Genomics 3, 59-66, 1988; Tawaragi Y., et al Biochem. Biophys. Res. Commun. 150, 89-96, 1988; Strausberg R. L., et al Proc. Natl. Acad. Sci. U.S.A. 99:16899-16903, 2002; WO2004063709; EP1439393 (Claim 7); WO2004044178 (Example 4); WO2004031238; WO2003042661 (Claim 12); WO200278524 (Example 2); WO200286443 (Claim 27; Page 427); WO200260317 (Claim 2);
  Accession: P40199; Q14920; EMBL; M29541; AAA59915.1. EMBL; M18728;
(19) MDP (DPEP1, Genbank accession no. BC017023) Proc. Natl. Acad. Sci. U.S.A. 99 (26):16899-16903 (2002)); WO2003016475 (Claim 1); WO200264798 (Claim 33; Page 85-87); JP05003790 (FIG. 6-8); WO9946284 (FIG. 9);
  Cross-references: MIM:179780; AAH17023.1; BC017023_1
(20) IL20Rα (IL20Rα, ZCYTOR7, Genbank accession no. AF184971); Clark H. F., et al Genome Res. 13, 2265-2270, 2003; Mungall A. J., et al Nature 425, 805-811, 2003; Blumberg H., et al Cell 104, 9-19, 2001; Dumoutier L., et al J. Immunol. 167, 3545-3549, 2001; Parrish-Novak J., et al J. Biol. Chem. 277, 47517-47523, 2002; Pletnev S., et al (2003) Biochemistry 42:12617-12624; Sheikh F., et al (2004) J. Immunol. 172, 2006-2010; EP1274274 (Example 11); US2004005320 (Example 5); WO2003029262 (Page 74-75); WO2003002717 (Claim 2; Page 63); WO200222153 (Page 45-47); US2002042366 (Page 20-21); WO200146261 (Page 57-59); WO200146232 (Page 63-65); WO9837193 (Claim 1; Page 55-59);
  Accession: □9UHF4; Q6UWA9; Q96SH8; EMBL; AF184971; AAF01320.1.
(21) Brevican (BCAN, BEHAB, Genbank accession no. AF229053) Gary S. C., et al Gene 256, 139-147, 2000; Clark H. F., et al Genome Res. 13, 2265-2270, 2003; Strausberg R. L., et al Proc. Natl. Acad. Sci. U.S.A. 99, 16899-16903, 2002; US2003186372 (Claim 11); US2003186373 (Claim 11); US2003119131 (Claim 1; FIG. 52); US2003119122 (Claim 1; FIG. 52); US2003119126 (Claim 1); US2003119121 (Claim 1; FIG. 52); US2003119129 (Claim 1); US2003119130 (Claim 1); US2003119128 (Claim 1; FIG. 52); US2003119125 (Claim 1); WO2003016475 (Claim 1); WO200202634 (Claim 1);
(22) EphB2R (DRT, ERK, Hek5, EPHT3, Tyro5, Genbank accession no. NM_004442) Chan, J. and Watt, V. M., (1991) Oncogene 6 (6), 1057-1061; Oncogene (1995) 10 (5):897-905; Annu. Rev. Neurosci. 21:309-345 (1998), Int. Rev. Cytol. 196:177-244 (2000)); WO 2003042661 (Claim 12); WO200053216 (Claim 1; Page 41); WO 2004065576 (Claim 1); WO 2004020583 (Claim 9); WO 2003004529 (Page 128-132); WO 200053216 (Claim 1; Page 42);
  Cross-references: MIM:600997; NP_004433.2; NM_004442_1
(23) ASLG659 (B7h, Genbank accession no. AX092328) US20040101899 (Claim 2); WO2003104399 (Claim 11); WO2004000221 (FIG. 3); US2003165504 (Claim 1); US2003124140 (Example 2); US2003065143 (FIG. 60); WO2002102235 (Claim 13; Page 299); US2003091580 (Example 2); WO200210187 (Claim 6; FIG. 10); WO200194641 (Claim 12; FIG. 7b); WO200202624 (Claim 13; FIG. 1A-1B); US2002034749 (Claim 54; Page 45-46); WO200206317 (Example 2; Page 320-321, Claim 34; Page 321-322); WO200271928 (Page 468-469); WO200202587 (Example 1; FIG. 1); WO200140269 (Example 3; Pages 190-192); WO200036107 (Example 2; Page 205-207); WO2004053079 (Claim 12); WO2003004989 (Claim 1); WO200271928 (Page 233-234, 452-453); WO 0116318;
(24) PSCA (Prostate stem cell antigen precursor, Genbank accession no. AJ297436) Reiter R. E., et al Proc. Natl. Acad. Sci. U.S.A. 95, 1735-1740, 1998; Gu Z., et al Oncogene 19, 1288-1296, 2000; Biochem. Biophys. Res. Commun. (2000) 275(3):783-788; WO2004022709; EP1394274 (Example 11); US2004018553 (Claim 17); WO2003008537 (Claim 1); WO200281646 (Claim 1; Page 164); WO2003003906 (Claim 10; Page 288); WO200140309 (Example 1; FIG. 17); US2001055751 (Example 1; FIG. 1b); WO200032752 (Claim 18; FIG. 1); WO9851805 (Claim 17; Page 97); WO9851824 (Claim 10; Page 94); WO9840403 (Claim 2; FIG. 1B);
  Accession: 043653; EMBL; AF043498; AAC39607.1.
(25) GEDA (Genbank accession No. AY260763); AAP14954 lipoma HMGIC fusion-partner-like protein /pid=AAP14954.1—Homo sapiens
Species: Homo sapiens (human)
WO2003054152 (Claim 20); WO2003000842 (Claim 1); WO2003023013 (Example 3, Claim 20); US2003194704 (Claim 45);
  Cross-references: GI:30102449; AAP14954.1; AY260763_1

(26) BAFF—R (B cell-activating factor receptor, BLyS receptor 3, BR3, Genbank accession No. NP_443177.1); NP_443177 BAFF receptor /pid=NP_443177.1—*Homo sapiens*
Thompson, J. S., et al Science 293 (5537), 2108-2111 (2001); WO2004058309; WO2004011611; WO2003045422 (Example; Page 32-33); WO2003014294 (Claim 35; FIG. 6B); WO2003035846 (Claim 70; Page 615-616); WO200294852 (Col 136-137); WO200238766 (Claim 3; Page 133); WO200224909 (Example 3; FIG. 3);
Cross-references: MIM:606269; NP_443177.1; NM_052945_1

(27) CD22 (B-cell receptor CD22-β isoform, Genbank accession No. NP-001762.1);
Stamenkovic, I. and Seed, B., Nature 345 (6270), 74-77 (1990); US2003157113; US2003118592; WO2003062401 (Claim 9); WO2003072036 (Claim 1; FIG. 1); WO200278524 (Example 2);
Cross-references: MIM:107266; NP_001762.1; NM_001771_1

(28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation) PROTEIN SEQUENCE Full mpggpgv . . . dvqlekp (1.226; 226 aa), pI: 4.84, MW: 25028 TM: 2 [P] Gene Chromosome: 19q13.2, Genbank accession No. NP_001774.10)
WO2003088808, US20030228319; WO2003062401 (Claim 9); US2002150573 (Claim 4, pages 13-14); WO9958658 (Claim 13, FIG. 16); WO9207574 (FIG. 1); U.S. Pat. No. 5,644,033; Ha et al (1992) J. Immunol. 148(5):1526-1531; Mueller et al (1992) Eur. J. Biochem. 22:1621-1625; Hashimoto et al (1994) Immunogenetics 40(4):287-295; Preud'homme et al (1992) Clin. Exp. Immunol. 90(1):141-146; Yu et al (1992) J. Immunol. 148(2) 633-637; Sakaguchi et al (1988) EMBO J. 7(11):3457-3464;

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia) PROTEIN SEQUENCE Full mnypltl . . . atslttf (1.372; 372 aa), pI: 8.54 MW: 41959 TM: 7 [P] Gene Chromosome: 11q23.3, Genbank accession No. NP_001707.1)
WO2004040000; WO2004015426; US2003105292 (Example 2); U.S. Pat. No. 6,555,339 (Example 2); WO200261087 (FIG. 1); WO200157188 (Claim 20, page 269); WO200172830 (pages 12-13); WO200022129 (Example 1, pages 152-153, Example 2, pages 254-256); WO9928468 (Claim 1, page 38); U.S. Pat. No. 5,440,021 (Example 2, col 49-52); WO9428931 (pages 56-58); WO9217497 (Claim 7, FIG. 5); Dobner et al (1992) Eur. J. Immunol. 22:2795-2799; Barella et al (1995) Biochem. J. 309:773-779;

(30) HLA-DOB (Beta subunit of MHC class II molecule (Ia antigen) that binds peptides and presents them to CD4+T lymphocytes) PROTEIN SEQUENCE Full mgsgwvp . . . vllpqsc (1.273; 273 aa, pI: 6.56 MW: 30820 TM: 1 [P] Gene Chromosome: 6p21.3, Genbank accession No. NP_002111.1)
Tonnelle et al (1985) EMBO J. 4(11):2839-2847; Jonsson et al (1989) Immunogenetics 29(6):411-413; Beck et al (1992) J. Mol. Biol. 228:433-441; Strausberg et al (2002) Proc. Natl. Acad. Sci. USA 99:16899-16903; Servenius et al (1987) J. Biol. Chem. 262:8759-8766; Beck et al (1996) J. Mol. Biol. 255:1-13; Naruse et al (2002) Tissue Antigens 59:512-519; WO9958658 (Claim 13, FIG. 15); U.S. Pat. No. 6,153,408 (Col 35-38); U.S. Pat. No. 5,976,551 (col 168-170); US6011146 (col 145-146); Kasahara et al (1989) Immunogenetics 30(1):66-68; Larhammar et al (1985) J. Biol. Chem. 260(26):14111-14119;

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability) PROTEIN SEQUENCE Full mgqagck . . . lephrst (1.422; 422 aa), pI: 7.63, MW: 47206 TM: 1 [P] Gene Chromosome: 17p13.3, Genbank accession No. NP_002552.2)
Le et al (1997) FEBS Lett. 418(1-2):195-199; WO2004047749; WO2003072035 (Claim 10); Touchman et al (2000) Genome Res. 10:165-173; WO200222660 (Claim 20); WO2003093444 (Claim 1); WO2003087768 (Claim 1); WO2003029277 (page 82);

(32) CD72 (B-cell differentiation antigen CD72, Lyb-2) PROTEIN SEQUENCE Full maeaity . . . tafrfpd (1.359; 359 aa), pI: 8.66, MW: 40225 TM: 1 [P] Gene Chromosome: 9p13.3, Genbank accession No. NP_001773.1)
WO2004042346 (Claim 65); WO2003026493 (pages 51-52, 57-58); WO200075655 (pages 105-106); Von Hoegen et al (1990) J. Immunol. 144(12):4870-4877; Strausberg et al (2002) Proc. Natl. Acad. Sci. USA 99:16899-16903;

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis) PROTEIN SEQUENCE Full mafdvsc . . . rwkyqhi (1.661; 661 aa), pI: 6.20, MW: 74147 TM: 1 [P] Gene Chromosome: 5q12, Genbank accession No. NP_005573.1) US2002193567; WO9707198 (Claim 11, pages 39-42); Miura et al (1996) Genomics 38(3):299-304; Miura et al (1998) Blood 92:2815-2822; WO2003083047; WO9744452 (Claim 8, pages 57-61); WO200012130 (pages 24-26);

(34) FCRH1 (Fc receptor-like protein 1, a putative receptor for the immunoglobulin Fc domain that contains C2 type Ig-like and ITAM domains, may have a role in B-lymphocyte differentiation) PROTEIN SEQUENCE Full mlprlll . . . vdyedam (1.429; 429 aa), pI: 5.28, MW: 46925 TM: 1 [P] Gene Chromosome: 1q21-1q22, Genbank accession No. NP_443170.1)
WO2003077836; WO200138490 (Claim 6, FIG. 18E-1-18-E-2); Davis et al (2001) Proc. Natl. Acad. Sci. USA 98(17):9772-9777; WO2003089624 (Claim 8); EP1347046 (Claim 1); WO2003089624 (Claim 7);

(35) IRTA2 (Immunoglobulin superfamily receptor translocation associated 2, a putative immunoreceptor with possible roles in B cell development and lymphomagenesis; deregulation of the gene by translocation occurs in some B cell malignancies) PROTEIN SEQUENCE Full mllwvil . . . assaphr (1.977; 977 aa), pI: 6.88 MW: 106468 TM: 1 [P] Gene Chromosome: 1q21, Genbank accession No. NP_112571.1)
WO2003024392 (Claim 2, FIG. 97); Nakayama et al (2000) Biochem. Biophys. Res. Commun. 277(1):124-127; WO2003077836; WO200138490 (Claim 3, FIG. 18B-1-18B-2);

Other exemplary monoclonal antibodies for use in the present invention which recognize tumor associated antigens include those listed in Table II below:

TABLE II

| Antigen Site Recognized | Monoclonal Antibodies | Reference |
|---|---|---|
| Lung Tumors | KS1/4 | N. M. Varki, et al., Cancer Res. 44: 681, 1984 |
|  | 534, F8; 604A9 | F. Cuttitta, et al., in: G. L. Wright (ed) Monoclonal Antibodies and Cancer, Marcel Dekker, Inc., NY., p. 161, 1984. |
| Squamous Lung | G1, LuCa2, LuCa3, LuCa4 | Kyoizumi et al., Cancer Res., 45: 3274, 1985. |
| Small Cell Lung Cancer | TFS-2 | Okabe et al., Cancer Res. 45: 1930, 1985. |
| Colon Cancer | 11.285.14 14.95.55 | G. Rowland, et al., Cancer Immunol.Immunother., 19: 1, 1985 |
|  | NS-3a-22, NS-10 | Z. Steplewski, et al., Cancer Res., 41: 2723, 1981. |
|  | NS-19-9, NS-33a |  |
|  | NS-52a, 17-1A |  |
|  | Erbitux ® |  |
| Carcinoembryonic | MoAb 35 or ZCE025 | Acolla, R. S. et al., Proc. Natl. Acad. Sci., (USA), 77: 563, 1980. |
| Melanoma | 9.2.27 | T. F. Bumol and R. A. Reisfeld, Proc. Natl. Acad. Sci., (USA), 79: 1245, 1982. |
| p97 | 96.5 | K. E. Hellstrom, et al., Monoclonal Antibodies and Cancer, loc. cit. p. 31. |
| Antigen T65 | T101 | Boehringer-Mannheim, P. O. Box 50816, Indianapolis, IN 46250 |
| Ferritin | Antiferrin | Boehringer-Mannheim, P.O. Box 50816, Indianapolis, IN 46250 |
|  | R24 | W. G. Dippold, et al., Proc. Natl. Acad. Sci. (USA), 77: 6114, 1980 |
| Neuroblastoma | P1 153/3 | R. H. Kennet and F. Gilbert, Science, 203: 1120, 1979. |
|  | MIN 1 | J. T. Kemshead in Monoclonal Antibodies and Cancer, loc. cit. p. 49. |
|  | UJ13A | Goldman et al., Pediatrics, 105: 252, 1984. |
| Glioma | BF7, GE2, CG12 | N. de Tribolet, et al., in Monoclonal Antibodies and Cancer, loc. cit. p. 81 |
| Ganglioside | L6 | I. Hellstrom et al. Proc. Natl Acad. Sci. (U.S.A) 83: 7059 (1986); U.S. Pat. Nos. 4,906,562, issued Mar. 6, 1990 and 4,935,495, issued Jun. 19, 1990. |
|  | Chimeric L6 | U.S. Ser. No. 07/923,244, (abandoned) filed Oct. 27, 1986, equivalent to PCT Patent Publication, WO 88/03145, published May 5, 1988. |
| Lewis Y | BR64 | U.S. Ser. Nos. 07/289,635 (abandoned) filed Dec. 22, 1988, and U.S. Ser. No. 07/443,696 (now U.S. Pat. No. 5,242,824) Nov. 29, 1989, equivalent to European Patent Publication, EP A 0 375 562, published Jun. 27, 1990, |
| fucosylated Lewis Y | BR96, Chimeric BR96 | U.S. Ser. Nos. 07/374,947 (abandoned) filed Jun. 30, 1989, and U.S. Ser. No. 07/544,246 (abandoned) filed Jun. 26, 1990, equivalent to PCT Patent Publication, WO 91/00295, published Jan. 10, 1991. |
| Breast Cancer | B6.2, B72.3 | D. Colcher, et al., in Monoclonal Antibodies and Cancer, loc. cit. p. 121. |
|  | Herceptin ® | Baselga et al., J. Clin. Oncol., 14: 737-744, 1996; U.S. Pat. No. 5,821,337 |
|  | Mylotarg ® |  |
| Osteogenic Sarcoma | 791T/48, 791T/36 | M. J. Embleton, ibid, p. 181 |
| Leukemia | CALL 2 | C. T. Teng, et al., Lancet, 1: 01, 1982 |
|  | anti-idiotype | R. A. Miller, et al., N. Eng. J. Med., 306: 517, 1982 |
| Ovarian Cancer | OC 125 | R. C. Bast, et al., J. Clin. Invest., 68: 1331, 1981. |
| Prostrate Cancer | D83.21, P6.2, Turp-27 | J. J. Starling, et al., in Monoclonal Antibodies and Cancer, loc. cit., p. 253 |
| Renal Cancer | A6H, D5D | P. H. Lange, et al., Surgery, 98: 143, 1985. |
| Non-Hodgkins lymphoma | Rituxan ® |  |

For other disclosure concerning tumor-associated antigens and specific antibodies thereto, see also: WO04/045516; WO03/000113; WO02/016429; WO02/16581; WO03/024392; WO04/016225; WO01/40309; and U.S. Provisional patent application Ser. No. 60/520,842 "COMPOSITIONS AND METHODS FOR THE TREATMENT OF TUMOR OF HEMATOPOIETIC ORIGIN", filed 17 Nov. 2003; all of which are incorporated herein by reference in their entirety.

Other exemplary antibodies and their abbreviations include: Herceptin® (trastuzumab)=full length, humanized antiHER2 (MW 145167), Herceptin F(ab')2=derived from antiHER2 enzymatically (MW 100000), 4D5=full-length, murine antiHER2, from hybridoma, rhu4D5=transiently expressed, full-length humanized antibody, rhuFab4D5=recombinant humanized Fab (MW 47738), 4D5Fc8=full-length, murine antiHER2, with mutated FcRn binding domain.

The antibody of the antibody-drug conjugates (ADC) of the invention may specifically bind to a receptor encoded by an ErbB gene. The antibody may bind specifically to an ErbB receptor selected from EGFR, HER2, HER3 and HER4. The ADC may specifically bind to the extracellular domain of the HER2 receptor and inhibit the growth of tumor cells which overexpress HER2 receptor. HERCEPTIN® (trastuzumab) selectively binds to the extracellular domain (ECD) of the human epidermal growth factor receptor2 protein, HER2 (ErbB2) (U.S. Pat. No. 5,821,337; U.S. Pat. No. 6,054,297; U.S. Pat. No. 6,407,213; U.S. Pat. No. 6,639,055; Coussens et al (1985) Science 230:1132-9; Slamon, et al (1989) Science 244:707-12). Trastuzumab is an IgG1 kappa antibody that contains human framework regions with the complementarity-determining regions (cdr) of a murine antibody (4D5) that binds to HER2. Trastuzumab binds to the HER2 antigen and thus inhibits the proliferation of human tumor cells that overexpress HER2 (Hudziak R M, et al (1989) Mol Cell Biol 9:1165-72; Lewis G D, et al (1993) Cancer Immunol Immunother; 37:255-63; Baselga J, et al (1998) Cancer Res. 58:2825-2831).

The antibody of the ADC may be a monoclonal antibody, e.g. a murine monoclonal antibody, a chimeric antibody, or a humanized antibody. A humanized antibody may be huMAb4D5-1, huMAb4D5-2, huMAb4D5-3, huMAb4D5-

4, huMAb4D5-5, huMAb4D5-6, huMAb4D5-7 or huMAb4D5-8 (Trastuzumab). The antibody may be an antibody fragment, e.g. a Fab fragment.

Known antibodies for the treatment or prevention of cancer can be conjugated as ADC. Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen can be obtained, e.g., from the GenBank database or a database like it, the literature publications, or by routine cloning and sequencing. Examples of antibodies available for the treatment of cancer include, but are not limited to, humanized anti-HER2 monoclonal antibody for the treatment of patients with metastatic breast cancer; RITUXAN® (rituximab; Genentech) which is a chimeric anti-CD20 monoclonal antibody for the treatment of patients with non-Hodgkin's lymphoma; OvaRex (AltaRex Corporation, MA) which is a murine antibody for the treatment of ovarian cancer; Panorex (Glaxo Wellcome, NC) which is a murine $IgG_{2a}$ antibody for the treatment of colorectal cancer; Cetuximab Erbitux (Imclone Systems Inc., NY) which is an anti-EGFR IgG chimeric antibody for the treatment of epidermal growth factor positive cancers, such as head and neck cancer; Vitaxin (Medlmmune, Inc., MD) which is a humanized antibody for the treatment of sarcoma; Campath UH (Leukosite, MA) which is a humanized $IgG_1$ antibody for the treatment of chronic lymphocytic leukemia (CLL); Smart MI95 (Protein Design Labs, Inc., CA) which is a humanized anti-CD33 IgG antibody for the treatment of acute myeloid leukemia (AML); LymphoCide (Immunomedics, Inc., NJ) which is a humanized anti-CD22 IgG antibody for the treatment of non-Hodgkin's lymphoma; Smart ID10 (Protein Design Labs, Inc., CA) which is a humanized anti-HLA-DR antibody for the treatment of non-Hodgkin's lymphoma; Oncolym (Techniclone, Inc., CA) which is a radiolabeled murine anti-HLA-Dr10 antibody for the treatment of non-Hodgkin's lymphoma; Allomune (BioTransplant, CA) which is a humanized anti-CD2 MAb for the treatment of Hodgkin's Disease or non-Hodgkin's lymphoma; Avastin (Genentech, Inc., CA) which is an anti-VEGF humanized antibody for the treatment of lung and colorectal cancers; Epratuzamab (Immunomedics, Inc., NJ and Amgen, CA) which is an anti-CD22 antibody for the treatment of non-Hodgkin's lymphoma; and CEAcide (Immunomedics, NJ) which is a humanized anti-CEA antibody for the treatment of colorectal cancer.

Hybrid or bifunctional antibodies may be derived, as noted, either biologically, by cell fusion techniques, or chemically, especially with cross-linking agents or disulfide bridge-forming reagents, and may be comprised of whole antibodies and/or fragments thereof (EP 0105360). Methods for obtaining such hybrid antibodies are disclosed, for example, in WO 83/03679, and EP 0217577, both of which are incorporated herein by reference. Bifunctional antibodies include those biologically prepared from a "polydoma" or "quadroma" or which are synthetically prepared with cross-linking agents such as bis-(maleimido)-methyl ether ("BMME"), or with other cross-linking agents familiar to those skilled in the art.

Immunoglobulin antibodies can recognize a tumor-associated antigen. As used, "immunoglobulin" may refer to any recognized class or subclass of immunoglobulins such as IgG, IgA, IgM, IgD, or IgE. The immunoglobulin can be derived from any species, such as human, murine, or rabbit origin. Further, the immunoglobulin may be polyclonal, monoclonal, or fragments. Such immunoglobulin fragments may include, for example, the Fab', F(ab')2, F v or Fab fragments, or other antigen recognizing immunoglobulin fragments. Such immunoglobulin fragments can be prepared, for example, by proteolytic enzyme digestion, for example, by pepsin or papain digestion, reductive alkylation, or recombinant techniques. The materials and methods for preparing such immunoglobulin fragments are well-known to those skilled in the art (Parham, (1983) J. Immunology, 131:2895; Lamoyi et al., (1983) J. Immunological Methods, 56:235; Parham, (1982) J. Immunological Methods, 53:133; and Matthew et al., (1982) J. Immunological Methods, 50:239).

In addition the immunoglobulin may be a single chain antibody ("SCA"). These may consist of single chain Fv fragments ("scFv") in which the variable light ("V L") and variable heavy ("V H") domains are linked by a peptide bridge or by disulfide bonds. Also, the immunoglobulin may consist of single V H domains (dAbs) which possess antigen-binding activity. See, e.g., G. Winter and C. Milstein, Nature, 349, 295 (1991); R. Glockshuber et al., Biochemistry 29, 1362 (1990); and, E. S. Ward et al., Nature 341, 544 (1989).

The immunoglobulin can be a chimeric antibody, e.g. humanized antibodies. Also, the immunoglobulin may be a "bifunctional" or "hybrid" antibody, that is, an antibody which may have one arm having a specificity for one antigenic site, such as a tumor associated antigen while the other arm recognizes a different target, for example, a hapten which is, or to which is bound, an agent lethal to the antigen-bearing tumor cell. Alternatively, the bifunctional antibody may be one in which each arm has specificity for a different epitope of a tumor associated antigen of the cell to be therapeutically or biologically modified. In any case, the hybrid antibodies may have dual specificity, with one or more binding sites specific for the hapten of choice or one or more binding sites specific for a target antigen, for example, an antigen associated with a tumor, an infectious organism, or other disease state.

One skilled in the art will recognize that a bifunctional-chimeric antibody can be prepared which would have the benefits of lower immunogenicity of the chimeric or humanized antibody, as well as the flexibility, especially for therapeutic treatment, of the bifunctional antibodies described above. Such bifunctional-chimeric antibodies can be synthesized, for instance, by chemical synthesis using cross-linking agents and/or recombinant methods of the type described above. In any event, the present invention should not be construed as limited in scope by any particular method of production of an antibody whether bifunctional, chimeric, bifunctional-chimeric, humanized, or an antigen-recognizing fragment or derivative thereof.

In addition, the invention encompasses within its scope immunoglobulins (as defined above) or immunoglobulin fragments to which are fused active proteins, for example, an enzyme of the type disclosed in Neuberger, et al., PCT application, WO86/01533, published Mar. 13, 1986. The disclosure of such products is incorporated herein by reference.

As noted, "bifunctional", "fused", "chimeric" (including humanized), and "bifunctional-chimeric" (including humanized) antibody constructions also include, within their individual contexts constructions comprising antigen recognizing fragments. Such fragments could be prepared by traditional enzymatic cleavage of intact bifunctional, chimeric, humanized, or chimeric-bifunctional antibodies. If, however, intact antibodies are not susceptible to such cleavage, because of the nature of the construction involved, the noted constructions can be prepared with immunoglobulin fragments used as the starting materials; or, if recombinant techniques are used, the DNA sequences, themselves, can be tailored to encode the desired "fragment" which, when expressed, can be combined in vivo or in vitro, by chemical or biological means, to prepare the final desired intact immunoglobulin "fragment". It is in this context, therefore, that the term "fragment" is used.

Furthermore, as noted above, the immunoglobulin (antibody), or fragment thereof, used in the present invention may be polyclonal or monoclonal in nature. The preparation of such polyclonal or monoclonal antibodies now is well known to those skilled in the art who, of course, are fully capable of producing useful immunoglobulins which can be used in the invention. See, e.g., G. Kohler and C. Milstein, Nature 256, 495 (1975). In addition, hybridomas and/or monoclonal antibodies which are produced by such hybridomas and which are useful in the practice of the present invention are publicly available from sources such as the American Type Culture Collection ("ATCC") 12301 Parklawn Drive, Rockville, Md. 20852 or, commercially, for example, from Boehringer-Mannheim Biochemicals, P.O. Box 50816, Indianapolis, Ind. 46250.

In an exemplary embodiment, the ligand-containing conjugate is derived from chimeric antibody BR96, "ChiBR96", disclosed in U.S. Ser. No. 07/544,246, filed Jun. 26, 1990, and which is equivalent to PCT Published Application, WO 91/00295, published Jan. 10, 1991. ChiBR96 is an internalizing murine/human chimeric antibody and is reactive, as noted, with the fucosylated Lewis Y antigen expressed by human carcinoma cells such as those derived from breast, lung, colon, and ovarian carcinomas. The hybridoma expressing chimeric BR96 and identified as ChiBR96 was deposited on May 23, 1990, under the terms of the Budapest Treaty, with the American Type Culture Collection ("ATCC"), 12301 Parklawn Drive, Rockville, Md. 20852. Samples of this hybridoma are available under the accession number ATCC HB 10460. ChiBR96 is derived, in part, from its source parent, BR96. The hybridoma expressing BR96 was deposited, on Feb. 21, 1989, at the ATCC, under the terms of the Budapest Treaty, and is available under the accession number HB 10036. Other hybridomas deposited with and accepted under the provisions of the Budapest Treaty by the American Type Culture Collection, 12301 Parklawn Drive, Rockville, Md. 20852 include HB8677, deposited Dec. 6, 1984, which produces L6 antibody, HB9895, deposited Nov. 16, 1988, which produces BR64 antibody, and HB9240, deposited Nov. 14, 1986, and HB9241, deposited Oct. 24, 1986, which produce chimeric L6 antibody. With respect to all of the foregoing hybridomas, all restrictions upon public access to the deposits will be irrevocably removed upon the grant of a patent on this application, the deposits will be replaced if viable samples cannot be dispensed by the depository, and the deposits will be maintained in a public depository for a period of thirty years after the date of deposit, or five years after the last request for a sample or for the effective life of the patent, whichever is longer. The desired hybridoma is cultured and the resulting antibodies are isolated from the cell culture supernatant using standard techniques now well known in the art. See, e.g., "Monoclonal Hybridoma Antibodies: Techniques and Applications", Hurell (ed.) (CRC Press, 1982).

Thus, as used "immunoglobulin" or "antibody" encompasses within its meaning all of the immunoglobulin/antibody forms or constructions noted above.

Preparation of Conjugates

The drug-ligand conjugates of the present invention may be constructed by attaching the drug moiety D to the ligand L through a linker made up of a peptide sequence incorporating a heterocyclic self-immolating moiety using established organic chemistry techniques from commercially available reagents. Heterocyclic linker compounds of Formulas Ia, IIa and IIIa are useful to prepare the drug-ligand conjugate compounds of Formula I. The terminii of Formulas Ia, IIa and IIIa bear protecting groups and reactive functional groups (X and Y) which are appropriate for covalent attachment to a drug moiety and a ligand through a series of reactions using known synthetic procedures.

Heterocyclic linker compounds have Formulas Ia, IIa and IIIa:

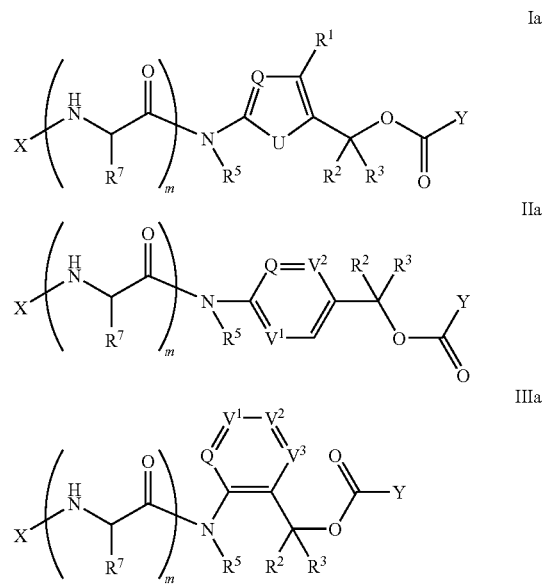

wHerein

U is O, S or $NR^6$;

Q is $CR^4$ or N;

$V^1$, $V^2$ and $V^3$ are independently $CR^4$ or N provided that for formula Ma and IIIb at least one of Q, $V^1$ and $V^2$ is N;

$R^1$, $R^2$, $R^3$ and $R^4$ are independently selected from H, F, Cl, Br, I, OH, $-N(R^5)_2$, $-N(R^5)_3^+$, $C_1$-$C_8$ alkylhalide, carboxylate, sulfate, sulfamate, sulfonate, $-SO_2R^5$, $-S(=O)R^5$, $-SR^S$, $-SO_2N(R^5)_2$, $-C(=O)R^5$, $-CO_2R^5$, $-C(=O)N(R^5)_2$, $-CN$, $-N_3$, $-NO_2$, $C_1$-$C_8$ alkoxy, $C_1$-$C_8$ halosubstituted alkyl, polyethyleneoxy, phosphonate, phosphate, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_1$-$C_{20}$ heterocycle, and $C_1$-$C_{20}$ substituted heterocycle; or when taken together, $R^2$ and $R^3$ form a carbonyl (=O), or spiro carbocyclic ring of 3 to 7 carbon atoms; and $R^5$ and $R^6$ are independently selected from H, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_1$-$C_{20}$ heterocycle, and $C_1$-$C_{20}$ substituted heterocycle;

where $C_1$-$C_8$ substituted alkyl, $C_2$-$C_8$ substituted alkenyl, $C_2$-$C_8$ substituted alkynyl, $C_6$-$C_{20}$ substituted aryl, and $C_2$-$C_{20}$ substituted heterocycle are independently substituted with one or more substituents selected from F, Cl, Br, I, OH, $-N(R^5)_2$, $-N(R^5)_3^+$, $C_1$-$C_8$ alkylhalide, carboxylate, sulfate, sulfamate, sulfonate, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, $-SO_2R^5$, $-S(=O)R^5$, $-SR^S$, $-SO_2N(R^5)_2$, $-C(=O)R^5$, $-CO_2R^5$, $-C(=O)N(R^5)_2$, $-CN$, $-N_3$, $-NO_2$, $C_1$-$C_8$ alkoxy, $C_1$-$C_8$ trifluoroalkyl, $C_1$-$C_8$ alkyl, $C_3$-$C_{12}$ carbocycle, $C_6$-$C_{20}$ aryl, $C_2$-$C_{20}$ heterocycle, polyethyleneoxy, phosphonate, and phosphate;

$R^7$ is the side chain of an amino acid and is optionally protected with a protecting group;

X and Y independently: are H; form a protecting group selected from Fmoc, Boc, carbobenzoxy (CBz), benzyhydryl, allyloxycarbonyl, and triphenylmethyl, or; form a reactive functional group selected from N-hydroxysuccinimide, para-nitrophenyl carbonate, para-nitrophenyl carbamate, pentafluorophenyl, haloacetamide, and maleimide; and m is 1, 2, 3, 4, 5, or 6.

In a general method, conjugates may be prepared starting from the enzymatically cleavable peptide sequence Zm (e.g. Phe-Lys, Val-Cit etc.) which is prepared using standard peptide synthesis. The cleavable peptide sequence is couple via its N-terminal amine to a spacer unit A (e.g. maleimidocaproyl-N-hydroxysuccinimide (MC-NHS) to form the intermediate represented by A-Zm The C-terminal carboxyl group of the cleavable peptide sequence is then reacted with the amine of an alcohol intermediate of a self-immolative moiety X (Formulas Ib, IIb or IIIb):

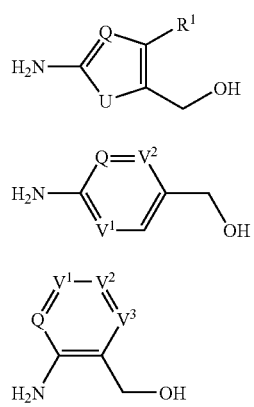

to make an amide bonded intermediate A-$Z_m$-X. In turn, this intermediate is reacted with a suitable reagent such as p-nitrophenyl chloroformate (PNPCF) to make the alcohol intermediate reactive with an amine, hydroxyl or sulfhydryl pending from a drug moiety D to give intermediate A-$Z_m$-X. This intermediate is then coupled to a ligand L (e.g. an antibody or receptor binding protein or peptide) by coupling the spacer unit A with a suitable functional group such as a sulfhydryl to give the final conjugate L-A-$Z_m$-X-D. The following is a representative general scheme for synthesizing conjugates of the invention wherein L, A, Z, X, m, D, Q, U and R have the meaning as described herein and functional groups in parenthesis represent part of the parent group (e.g. A-COOH).

General Scheme I

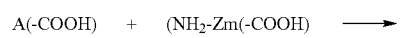

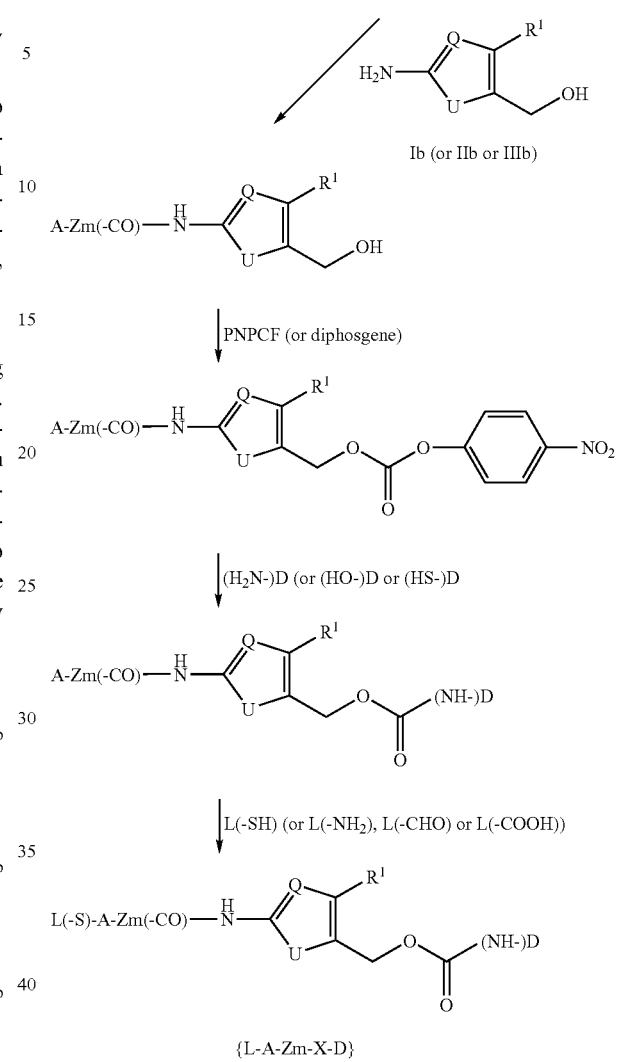

Alternatively, a functional amine group on drug moiety D is first reacted with diphosgene $Cl_3COC(O)$—Cl and/or CDI (N,N-carbonyldiimidazole) and subsequently reacted with the alcohol intermediate Ib (or IIb or Mb) to form a carbamate linkage between the heterocyclic self-immolative unit X and drug moiety D.

In an alternative general synthetic method a carboxylic ester intermediate Ic (or IIc or IIIc):

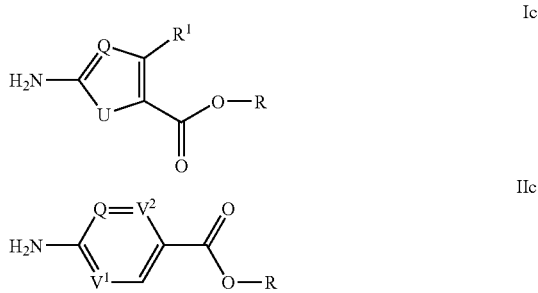

-continued

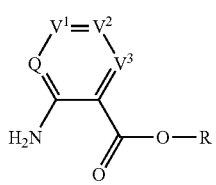
IIIc where R is alkyl, such as methyl, ethyl, isopropyl, is first coupled to the cleavable peptide sequence $Z_m$ which is converted to the corresponding alcohol and then reacted with para-nitrophenylchloroformate (PNPCl) for coupling with a functional group on the drug moiety. The resulting intermediate $Z_m$-X-D is coupled via an amide bond to a suitable spacer unit A to form intermediate A-$Z_m$-X-D which is coupled to the ligand moiety L to give the final conjugate compound (General Scheme II).

General Scheme II

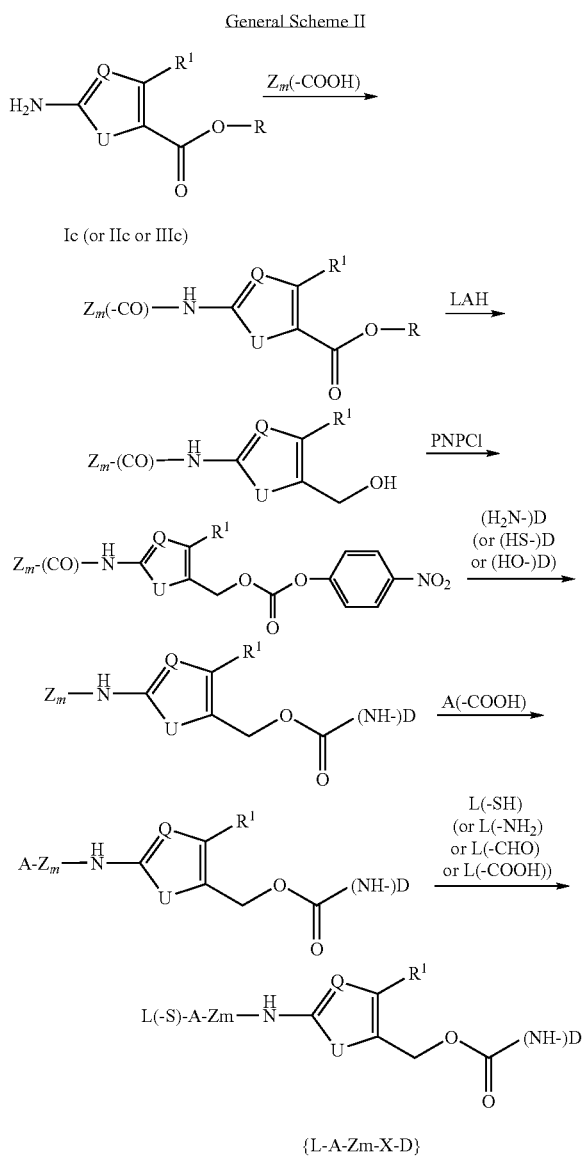

{L-A-Zm-X-D}

An alternative embodiment employs a functional amine group on drug moiety D to be first reacted with diphosgene Cl$_3$COC(O)Cl and/or CDI and subsequently reacted with the alcohol intermediates, Ib, IIb or IIIb, to form a carbamate linkage between the self-immolative unit X and drug moiety D. Intermediates Ib, IIb, IIIb, Ic, IIe and IIIc shown in General schemes I and II are commercially available or may be prepared using established synthetic techniques from reagents that are commercially available.

It will be understood that in describing these general examples, where a formula, e.g. Formula Ia is named, a phrase such as "or IIa or IIIa" indicates that compounds of Formulas IIa and or IIIa may also be reacted in a similar manner as described.

An exemplary process for preparing the conjugates of the invention in which the ligand is an antibody includes, a solution of the antibody in a phosphate buffer or PBS is treated with a solution of dithiothreitol (DTT) at about 25-45° C., for about 1-10 hours under N$_2$. The solution is then diafiltered against phosphate buffered saline (PBS) for ½ to 12 hours depending on the size of diafiltration cell and volume of solution under N$_2$, until the effluent is free of SH groups, then treated with the appropriate amount of the peptide-self-immolative moiety-drug intermediate represented by the formula [A-$Z_m$-X]-D (based on the number of SH groups in the MAb (determined by Ellman titration)] in distilled water, at 0±10° C. for 15 minutes to 8 hours. The solution is then dialyzed against PBS for about 24 hours, at room temperature, then filtered and the filtrate is shaken for 15 minutes to 8 hours at room temperature with Biobeads, followed by another filtration. In a similar manner, conjugates may be prepared in which the ligand is a protein or peptide incorporating a sulfhydryl group such as a Cys residue side chain.

EXAMPLES

General Procedures

NMR was obtained on a Varian-300 spectrometer, with $^1$H 300 MHz in deuterated DMSO unless otherwise specified. All chemical shifts are referenced to tetramethylsilane. Mass spectra were determined on a PE SCIEX, API 2000 LC-MS spectrometer. Solutions in organic solvents were dried with anhydrous Na$_2$SO$_4$. Solvents were evaporated under reduced pressure on a Buchi rotary evaporator. TLC was carried out on glass-backed silica gel plates (Merck 60 F254) with visualization of components by UV light (254 nm). Flash column chromatography was performed on silica gel (Merck 230-400 mesh).

DCM refers to dichloromethane; DIEA refers to diisopropylethylamine; CDI refers to 1,1'-carbonyldiimidazole; RT refers to room temperature; HBTU refers to O-benzotriazole-N,N,N', N'-tetramethyluroniumhexafluorophosphate.

Example 1

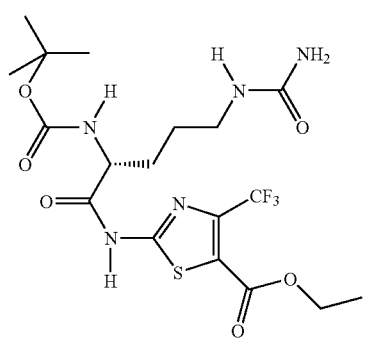

1A 8.6 grams of Boc-Citrulline was dissolved in 250 ml of DMF. The solution was added 7.2 mL of DIEA and 6.7-grams of CDI. After stirred at RT for 30 min, the solution was added 5 grams of ethyl 2-amino-4-(trifluoromethyl)-5-thiazolecarboxylate (Matrix Scientific, Columbia S.C. USA). The reaction was quenched after additional 2 hours at RT by addition of 25 ml of water. The mixture was diluted with 250 ml of EtOAc. The organic layer was washed with 1N HCl, Brine and worked up as described in General Procedure. pure title compound (1A) was obtained by purification on a fresh silica gel column eluted with 5% MeOH in DCM (5.6 grams, yield 54%).

Example 2

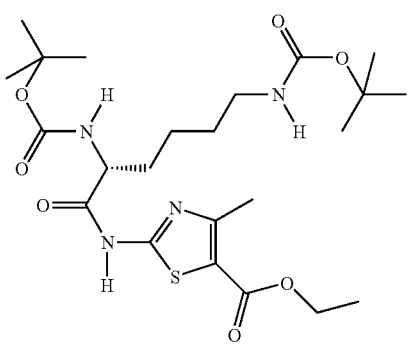

1B

Ethyl 2-amino-4-methyl thiazole-5-carboxylate (50 mg, Avocado Research Chemicals LTD), 140 mg of N,N-Di-Boc-lysine, 95 µl of DIEA, and 153 mg of HBTU were dissolved in 1.5 ml of DMF. After stiffing at RT for 48 hours, the reaction was quenched by addition of 0.5 ml water and diluted with 40 ml of EtOAc. The organic layer was washed with 1N HCl, brine and worked-up as described in General Procedure. Pure title compound (1B) was obtained by purification on a fresh silica gel column eluted with 30% EtOAc in hexane (30 mg, yield 22%).

Example 3

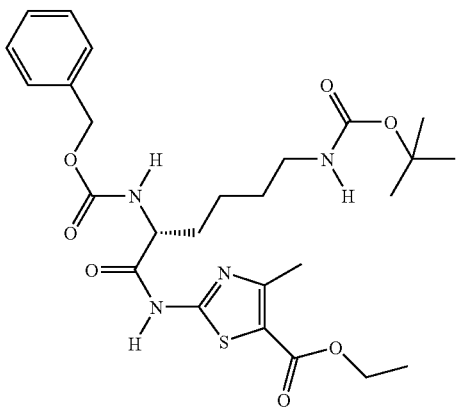

1C

Ethyl 2-amino-4-methyl thiazole-5-carboxylate (500 mg), 1.5 grams of N-Cbz-N-Boc-lysine, 0.99 ml of DIEA, and 2.0 grams of HBTU were dissolved in 15 ml DMF. After stirring at RT for 48 hours, the reaction was quenched by addition of 0.5 ml of water and diluted with 40 ml of EtOAc. The organic layer was washed with 1N HCl, brine and worked-up as described in General Procedure. Pure title compound (1C) was obtained by purification on a fresh silica gel column eluted with 30% EtOAc in Hexane (1.3 grams, 88%).

Example 4

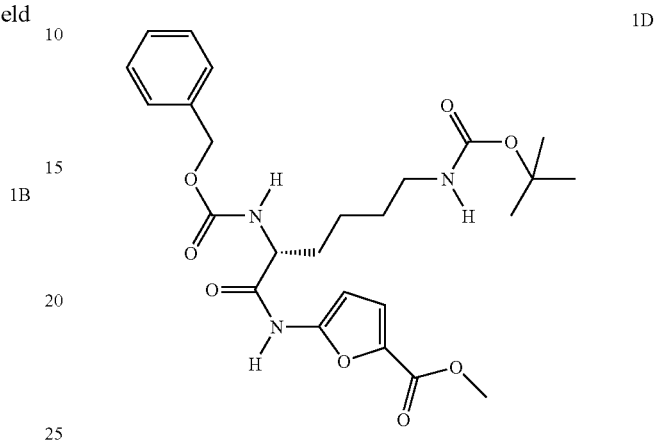

1D

I. A solution of 100 mg of methyl 5-nitro-2-furoate (Lancaster Synthesis, Windham, N.H., USA) in 20 ml of EtOAc was stirred with 20 mg of Pd/C (10%) under one atmospheric pressure of hydrogen gas. After at RT for 2 hours, the mixture was filtered through a celite pad and concentrated. Pure methyl 5-amino-2-furoate was obtained by purification on a fresh silica gel column eluted with 30% EtOAc in hexane.

II. The 50 mg of methyl 5-amino-2-furoate, 202 mg of N-Cbz-N-Boc-lysine, 123 ul of DIEA, and 202 mg of HBTU were dissolved in 1.5 ml DMF. After stirring at RT for 48 hours, the reaction was quenched by addition of 0.5 ml of water and diluted with 40 ml of EtOAc. The organic layer was washed with 1N HCl and brine, and worked-up as described in General Procedure. Pure title compound (1D) was obtained by purification on a fresh silica gel column eluted with 30% EtOAc in Hexane (56 mg, 31%).

Example 5

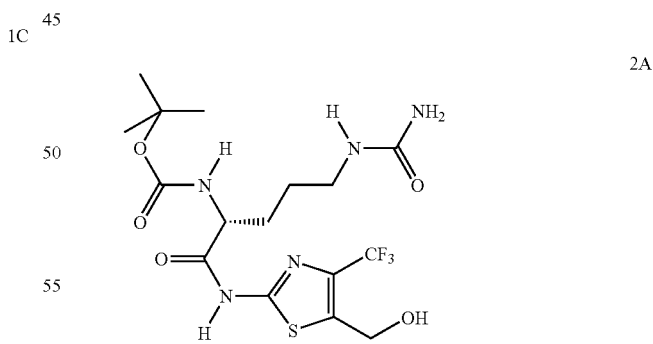

2A 3 grams of 1A was dissolved in 90 ml of THF. The solution was added 12 ml of lithium aluminide hydride (LAH, 1.0M solution in THF) at 0° C. After stiffing at 0° C. for 2 hours, the reaction was quenched by addition of 10 ml of water, diluted with 250 ml of EtOAc and filtered through a celite pad. The organic layer was washed with brine and worked up as described in General Procedure. Pure title compound (2A) was obtained by purification on a fresh silica gel column eluted with 5% MeOH in DCM (2.2 grams yield 80%).

Example 6

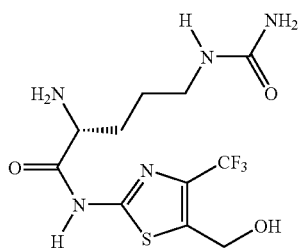

3A

Compound 2A (1.5 gm) was dissolved in 45 ml methanol. To the solution was added 8 ml of HCl in dioxane (4.0M). After stiffing at room temperature (RT) for 2 hours, the solution was concentrated down at a rotary evaporator under reduced pressure. The crude product was dried under vacuum for additional 18 hours at RT and used for next reaction without further purification.

Example 7

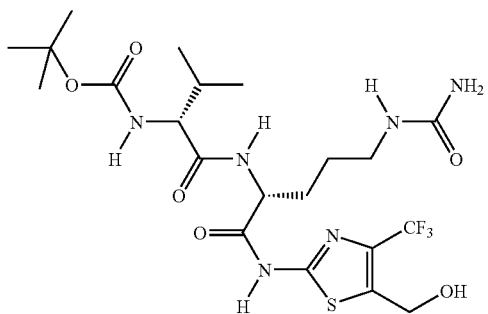

4A

Compound 3A (1.2 gm), 1.1 grams of Boc-valine, 1.4 ml of DIEA, and 3.3 grams of HBTU were dissolved in 36 ml DMF. After stiffing at RT for 18 hours, the reaction was quenched by addition of 5 ml of water and diluted with 400 ml of EtOAc. The organic layer was washed with Brine and worked up as described in General Procedure. Pure title compound (4A) was obtained by purification on a fresh silica gel column eluted with 10% MeOH in DCM (1.4 grams, yield 75%).

Example 8

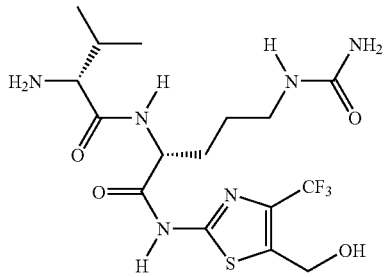

5A

Compound 4A (1.4 grams) was dissolved in 40 ml methanol. To the solution was added 10 ml of HCl in dioxane (4.0M). After stirring at RT for 2 hours, the solution was concentrated down at a rotary evaporator under reduced pressure. The crude product was dried under vacuum for additional 18 hours at RT and used for next reaction without further purification.

Example 9

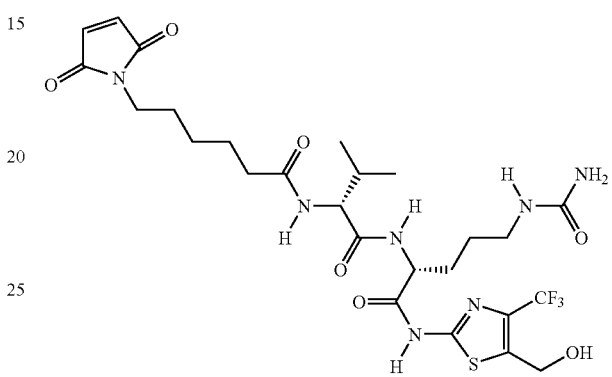

6A

Compound 5A (1.1 grams), 0.8 grams of maleimidocaproic acid, 1.1 ml of DIEA, and 2.5 grams of HBTU were dissolved in 33 ml DMF. After stirring at RT for 18 hours, the reaction was quenched by addition of 5 ml of water and diluted with 400 ml of EtOAc. The organic layer was washed with brine and worked up as described in General Procedure. Pure title compound (6A) was obtained by purification on a fresh silica gel column eluted with 10% MeOH in DCM (1.4 grams, yield 89%).

Example 10

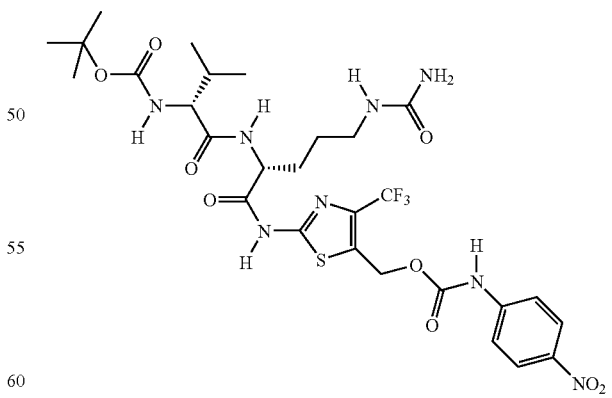

7A

Compound 4A (50 mg) was dissolved in 0.5 ml of THF and DCM (1:1). To the solution was added 30 mg of 4-nitrophenyl isocyanate. After stiffing at RT for 48 hours, the mixture was directly charged to a silica gel column eluted with 5% MeOH in DCM to give the pure title compound (7A).

Example 11

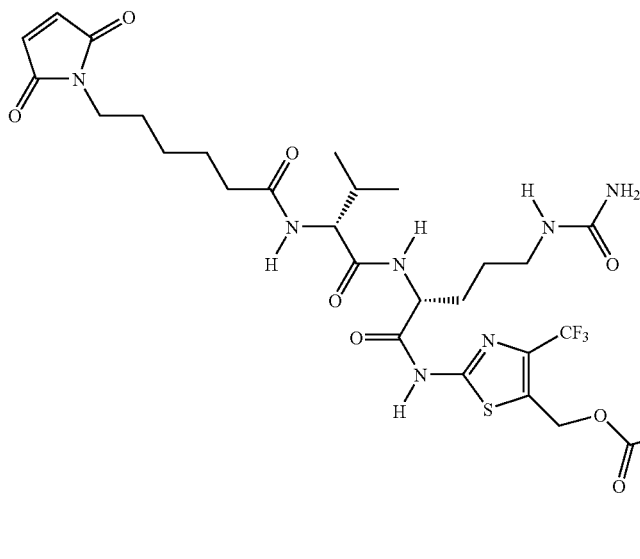

7B

Compound 6A (30 mg) was dissolved in 0.5 ml of THF and DCM (1:1). The solution was added 30 mg of 4-nitrophenyl isocyanate. After stirring at RT for 48 hours, the mixture was directly charged to a silica gel column eluted with 5% MeOH in DCM to give the pure title compound (7B).

Example 12

Cathepsin B cleavage of 7A and 7B

Model compounds with a cleavable peptide unit and a heterocyclic self-immolative moiety, and conjugates of Formula I can be tested for stability and kinetics of enzymatic hydrolysis by the methods of de Groot, et al (1999) J. Med. Chem. 42(25):5277-5283.

To demonstrate the ability of the conjugates of the invention to function i.e. to liberate an underivatized drug in the presence of an intracellular enzyme, intermediates 7A and 7B were exposed to cathepsin B and the resulting cleavage product, para-nitrophenylamine was detected. FIG. 2 is a schematic representation of the cleavage mechanism.

A cathepsin B (CalBiochem) stock solution at 28.4 μM was diluted to 1 μM in 50 mM sodium acetate buffer pH 7.5, containing 2 mM DTT. Activation was carried out at 37° C. for 15 minutes.

Substrate compounds 7A and 7B were diluted to 100 μM in 50 mM sodium acetate buffer pH 5. Activated cathepsin B was added to a final concentration of 100 nM and the cleavage reaction was carried out at 37° C. for 16 hrs in the presence or absence of 1 mM cysteine.

Reversed-phase separation of cleavage products was carried out using an Agilent 1100 HPLC system. UV signal was monitored at 214, 254 and 380 nm A Poroshell 300SB-C18 column (No. 660750-902) from Agilent was used. Mobile phases A and B contained 0.05% TFA aqueous solution and $CH_3CN$ containing 0.05% TFA, respectively. Aliquots (50 μl) of the untreated control samples; the samples treated with cathepsin B alone, and the samples treated with cysteine plus cathepsin B, were injected onto the column and eluted with a linear gradient from 0-50% B in 21 minutes. The cleavage product of 4-nitroaniline was monitored by its distinct absorbance at 380 nm in the void volume. The cleavage reactions with 7A and 7B were each complete as evidenced by the complete disappearance of 7A and 7B.

I claim:
1. A heterocyclic linker compound selected from the group consisting of Formulas IIa and IIIa:

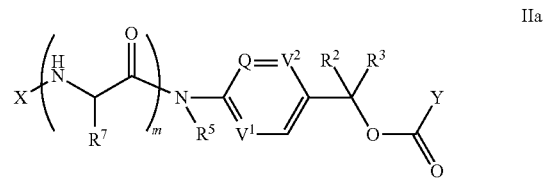

IIa

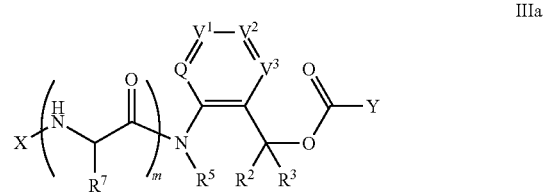

IIIa wherein
Q is $CR^4$ or N;
$V^1$, $V^2$ and $V^3$ are independently $CR^4$ or N provided that for formula IIa and IIIa at least one of Q, $V^1$ and $V^2$ is N;
$R^2$, $R^3$ and $R^4$ are independently selected from the group consisting of H, F, Cl, Br, I, OH, $—N(R^5)_2$, $—N(R^5)_3^+$, $C_1$-$C_8$ alkylhalide, carboxylate, sulfate, sulfamate, sulfonate, $—SO_2R^5$, $—S(=O)R^5$, $—SR^5$, $—SO_2N(R^5)_2$, $—C(=O)R^5$, $—CO_2R^5$, $—C(=O)N(R^5)_2$, $—CN$, $—N_3$, $—NO_2$, $C_1$-$C_8$ alkoxy, $C_1$-$C_8$ halosubstituted alkyl, polyethyleneoxy, phosphonate, phosphate, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_1$-$C_{20}$ heterocycle, and $C_1$-$C_{20}$ substituted heterocycle; or when taken together, $R^2$ and $R^3$ form a carbonyl (=O), or spiro carbocyclic ring of 3 to 7 carbon atoms; and $R^5$ and $R^6$ are independently selected from the group consisting of H, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_1$-$C_{20}$ heterocycle, and $C_1$-$C_{20}$ substituted heterocycle;

where $C_1$-$C_8$ substituted alkyl, $C_2$-$C_8$ substituted alkenyl, $C_2$-$C_8$ substituted alkynyl, $C_6$-$C_{20}$ substituted aryl, and $C_2$-$C_{20}$ substituted heterocycle are independently substituted with one or more substituents selected from the group consisting of F, Cl, Br, I, OH, —N($R^5$)$_2$, —N($R^5$)$_3^+$, $C_1$-$C_8$ alkylhalide, carboxylate, sulfate, sulfamate, sulfonate, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, —SO$_2$$R^5$, —S(=O)$R^5$, —S$R^5$, —SO$_2$N($R^5$)$_2$, —C(=O)$R^5$, —CO$_2$$R^5$, —C(=O)N($R^5$)$_2$, —CN, —N$_3$, —NO$_2$, $C_1$-$C_8$ alkoxy, $C_1$-$C_8$ trifluoroalkyl, $C_1$-$C_8$ alkyl, $C_3$-$C_{12}$ carbocycle, $C_6$-$C_{20}$ aryl, $C_2$-$C_{20}$ heterocycle, polyethyleneoxy, phosphonate, and phosphate;

$R^7$ is the side chain of an amino acid and is optionally protected with a protecting group;

X and Y independently: are H; form a protecting group selected from the group consisting of Fmoc, Boc, carbobenzoxy (CBz), benzyhydryl, allyloxycarbonyl, and triphenylmethyl, or; form a reactive functional group selected from the group consisting of N-hydroxysuccinimide, para-nitrophenyl carbonate, para-nitrophenyl carbamate, pentafluorophenyl, haloacetamide, and maleimide; and m is 1, 2, 3, 4, 5, or 6.

2. A drug-ligand conjugate compound comprising a cell-specific ligand and a drug moiety conjugated by a linker wherein said linker comprises a heterocyclic self-immolative moiety selected from the group consisting of Formulas II and III

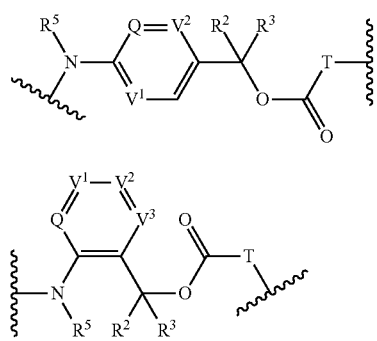

where the wavy lines indicate the covalent attachment sites to the cell-specific ligand and the drug moiety, and wherein:

Q is C$R^4$ or N;

$V^1$, $V^2$ and $V^3$ are independently C$R^4$ or N provided that at least one of Q, $V^1$ and $V^2$ is N;

T is NH, N$R^6$, O or S pending from said drug moiety;

$R^2$, $R^3$ and $R^4$ are independently selected from the group consisting of H, F, Cl, Br, I, OH, —N($R^5$)$_2$, —N($R^5$)$_3^+$, $C_1$-$C_8$ alkylhalide, carboxylate, sulfate, sulfamate, sulfonate, —SO$_2$$R^5$, —S(=O)$R^5$, —S$R^5$, —SO$_2$N($R^5$)$_2$, —C(=O)$R^5$, —CO$_2$$R^5$, —C(=O)N($R^5$)$_2$, —CN, —N$_3$, —NO$_2$, $C_1$-$C_8$ alkoxy, $C_1$-$C_8$ halosubstituted alkyl, polyethyleneoxy, phosphonate, phosphate, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_1$-$C_{20}$ heterocycle, and $C_1$-$C_{20}$ substituted heterocycle; or when taken together, $R^2$ and $R^3$ form a carbonyl (=O), or spiro carbocyclic ring of 3 to 7 carbon atoms; and $R^5$ and $R^6$ are independently selected from the group consisting of H, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_1$-$C_{20}$ heterocycle, and $C_1$-$C_{20}$ substituted heterocycle;

where $C_1$-$C_8$ substituted alkyl, $C_2$-$C_8$ substituted alkenyl, $C_2$-$C_8$ substituted alkynyl, $C_6$-$C_{20}$ substituted aryl, and $C_2$-$C_{20}$ substituted heterocycle are independently substituted with one or more substituents selected from the group consisting of F, Cl, Br, I, OH, —N($R^5$)$_2$, —N($R^5$)$_3^+$, $C_1$-$C_8$ alkylhalide, carboxylate, sulfate, sulfamate, sulfonate, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, —SO$_2$$R^5$, —S(=O)$R^5$, —S$R^5$, —SO$_2$N($R^5$)$_2$, —C(=O)$R^5$, —CO$_2$$R^5$, —C(=O)N($R^5$)$_2$, —CN, —N$_3$, —NO$_2$, $C_1$-$C_8$ alkoxy, $C_1$-$C_8$ trifluoroalkyl, $C_1$-$C_8$ alkyl, $C_3$—$C_{12}$ carbocycle, $C_6$-$C_{20}$ aryl, $C_2$-$C_{20}$ heterocycle, polyethyleneoxy, phosphonate, and phosphate.

3. The drug-ligand conjugate compound of claim 2 having Formula IV:

$$L\text{-}[A_n\text{-}Z_m\text{-}X\text{-}D]_p \qquad \text{IV}$$

wherein

L is a cell-specific ligand;

A is a Spacer unit;

Z is an Amino Acid;

X is a heterocyclic self-immolative moiety selected from the group consisting of Formula II and III;

D is a drug moiety;

m is 1, 2, 3, 4, 5 or 6;

n is 0 or 1; and p is 1, 2, 3, 4, 5, 6, 7 or 8.

4. The drug-ligand conjugate compound of claim 3, wherein X is Formula II.

5. The drug-ligand conjugate compound of claim 4, wherein Q is N; $V^1$ is CH; and $V^2$ is CH.

6. The drug-ligand conjugate compound of claim 4, wherein Q is CH; $V^1$ is CH; and $V^2$ is N.

7. The drug-ligand conjugate compound of claim 4, wherein Q is N; $V^1$ is CH; and $V^2$ is N.

8. The drug-ligand conjugate compound of claim 4, wherein Q is N; and $V^1$ is N; and $V^2$ is N.

9. The drug-ligand conjugate compound of claim 4, wherein Q is N; $V^1$ is N; and $V^2$ is CH.

10. The drug-ligand conjugate compound of claim 4, wherein T is N or NH.

11. The drug-ligand conjugate compound of claim 3, wherein X is Formula III.

12. The drug-ligand conjugate compound of claim 11, wherein Q is N; and $V^1$, $V^2$ and $V^3$ are each CH.

13. The drug-ligand conjugate compound of claim 11, wherein Q is CH; and $V^1$, $V^2$ and $V^3$ are each CH.

14. The drug-ligand conjugate compound of claim 11, wherein T is N or NH.

15. The drug-ligand conjugate compound of claim 3 wherein m is 1, and Z is selected from the group consisting of alanine, 2-amino-2-cyclohexylacetic acid, 2-amino-2-phenylacetic acid, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, γ-aminobutyric acid, α,α-dimethyl γ-aminobutyric acid, β,β-dimethyl γ-aminobutyric acid, ornithine, citrulline; and protected forms thereof.

16. The drug-ligand conjugate compound of claim 3, wherein m is 2, and $Z_m$ is a dipeptide selected from the group consisting of glycine-glycine, alanine-phenylalanine, phenylalanine-lysine, valine-citrulline and valine-lysine.

17. The drug-ligand conjugate compound of claim 3, wherein n is 1, and A is attached to a Cys residue of L which is an antibody.

18. The drug-ligand conjugate compound of claim 3,

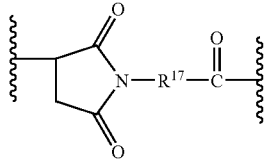

wherein n is 1, and A has the structure:
where the wavy lines indicate the covalent attachment sites to a sulfur atom of L and to $Z_m$, and wherein $R^{17}$ is selected from the group consisting of $(CH_2)_r$, $C_3$-$C_8$ carbocyclyl, $O(CH_2)_r$, arylene, $(CH_2)_r$-arylene, -arylene-$(CH_2)_r$—, $(CH_2)_r$—$(C_3$-$C_8$ carbocyclyl), $(C_3$-$C_8$ carbocyclyl)—$(CH_2)_r$, $C_3$-$C_8$ heterocyclyl, $(CH_2)_r$—$(C_3$-$C_8$ heterocyclyl), —$(C_3$-$C_8$ heterocyclyl)—$(CH_2)_r$—, —$(CH_2)_rC(O)NR^b(CH_2)_r$—, —$(CH_2CH_2O)_r$—, —$(CH_2CH_2O)_r$—$CH_2$—, —$(CH_2)_rC(O)NR^b(CH_2CH_2O)_r$—, —$(CH_2)_rC(O)NR^b(CH_2CH_2O)_r$—$CH_2$—, —$(CH_2CH_2O)_rC(O)NR^b(CH_2CH_2O)_r$—, —$(CH_2CH_2O)_rC(O)NR^b(CH_2CH_2O)_r$—$CH_2$—, and —$(CH_2CH_2O)_rC(O)NR^b(CH_2)_r$—; where r is independently an integer ranging from 1-10.

19. The drug-ligand conjugate compound of claim 3, wherein D is an auristatin drug moiety.

* * * * *